US011359181B2

(12) United States Patent
Romero et al.

(10) Patent No.: US 11,359,181 B2
(45) Date of Patent: Jun. 14, 2022

(54) BACTERICIDE COMPOSITION BASED ON A MIXTURE OF BACTERIOPHAGES FOR THE CONTROL OF BLACK PLAGUE IN PLANTS OR PARTS THEREOF, PREFERABLY THE WALNUT, CAUSED BY XANTHOMONAS ARBORICOLA PV. JUGLANDIS; PREPARATION METHOD AND APPLICATION

(71) Applicant: UNIVERSIDAD DE CHILE, Santiago (CL)

(72) Inventors: Jaime Romero, Santiago (CL); Gaston Higuera, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 552 days.

(21) Appl. No.: 16/067,361

(22) PCT Filed: Dec. 29, 2016

(86) PCT No.: PCT/CL2016/050078
§ 371 (c)(1),
(2) Date: Dec. 18, 2018

(87) PCT Pub. No.: WO2017/113029
PCT Pub. Date: Jul. 6, 2017

(65) Prior Publication Data

US 2019/0116799 A1 Apr. 25, 2019

(30) Foreign Application Priority Data

Dec. 29, 2015 (CL) .................................. 3754-2015

(51) Int. Cl.
*A01N 63/00* (2020.01)
*A01N 25/22* (2006.01)
*C12N 7/00* (2006.01)
*A01N 63/40* (2020.01)

(52) U.S. Cl.
CPC ............... *C12N 7/00* (2013.01); *A01N 25/22* (2013.01); *A01N 63/40* (2020.01); *C12N 2795/00031* (2013.01); *C12N 2795/00051* (2013.01)

(58) Field of Classification Search
CPC ........ A01N 63/00; A01N 25/22; A01N 63/40; C12N 7/00; C12N 2795/00031; C12N 2795/00051; C12N 2795/10021; C12N 2795/10031
See application file for complete search history.

(56) References Cited

PUBLICATIONS

Dora Domotor, et al; "Comparative analysis of two bacteriophages of Xanthomonas arboricola pv. juglandis", Science Digest Infection, Genetics and Evolution, vol. 43, pp. 371-377; available online Jun. 6, 2016.
Andrew Pitman, et al; "Advances in Bacteriophage-Mediated Control of Plant Pathogens", International Journal of Microbiology; Aug. 2012; 12 pages.
Jay Ram Lamichhane; "Xanthomonas arboricola Diseases of Stone Fruit, Almond, and Walnut Trees: Progress Toward Understanding and Management", Plant Disease, vol. 98. No. 12; Sep. 2014; 8 pages.
D.L. McNeil, et al; Bacteriophages: A Potential Biocontrol Agent Against Walnut Blight (Xanthomonas Campestris PV Juglandis), New Zealand Plant Protection, Published Aug. 1, 2001; vol. 54, 5 pages.
Julio Retamales, et al; "Complete Genome Sequences of Lytic Bacteriophages of Xanthomonas arboricola pv. juglandis", Genome Announcements May/Jun. 2016; vol. 4, Issue 3 e00336-16.
Sandra Romero-Suarez, et al; "Isolation and characterization of bacteriophages infecting Xanthomonas arboricola pv. juglandis, the causal agent of walnut blight disease", World J Microbiol Biotechnol 2012; vol. 28, 1917-1927, published online Jan. 7, 2012.
Maciej Zaczek; "Phages in the global fruit and vegetable industry", Journal of Applied Mcrobiology, Nov. 2014; 21 pages.
Office Action dated Dec. 29, 2015; Appln. No. 201503754.
Office Action dated Jun. 8, 2018; Appln. No. 201503754.
International Search Report dated Apr. 21, 2017; PCT/CL2016/050078.

*Primary Examiner* — Kade Ariani
(74) *Attorney, Agent, or Firm* — Lucas & Mercanti, LLP

(57) ABSTRACT

The invention relates to a bactericide composition based on bacteriophages for the control of black plague in plants or parts thereof, preferably walnuts, a preparation method and application. The invention provides methods for the isolation, propagation and application of bacteriophages against phytopathogens affecting trees/plants that are of commercial interest for their fruit, flowers etc., for the prevention, treatment or reduction of signs, in particular, for *Xanthomonas A.* pv *juglandis* in walnuts.

11 Claims, 16 Drawing Sheets

Specification includes a Sequence Listing.

| Bacteria and procedence | | | Seven selected phages | | | | | | |
|---|---|---|---|---|---|---|---|---|---|
| Location | Region | Xaj | Φ6 | ΦM2-2 | ΦM4-109a | Φ36 | ΦM307-70a | ΦM310-91a | Φ4.1 |
| Quillón | VIII | 1 | | | | | | | |
| Aguas Buenas | VIII | 2 | | | | | | | |
| Quillón | VIII | 4 | | | | | | | |
| Quillón | VIII | 5 | | | | | | | |
| Aguas Buenas | VIII | 8 | | | | | | | |
| Aguas Buenas | VIII | 10 | | | | | | | |
| Quillón | VIII | 13 | | | | | | | |
| Aguas Buenas | VIII | 16 | | | | | | | |
| Aguas Buenas | VIII | 22 | | | | | | | |
| Sin info | VIII | 33 | | | | | | | |
| Quillón | VIII | 35 | | | | | | | |
| Sin info | VIII | 38 | | | | | | | |
| Quillón | VIII | 52 | | | | | | | |
| Cepario | Cepario | 762 | | | | | | | |
| Cepario | Cepario | 830 | | | | | | | |
| La Suiza | VII | 36B | | | | | | | |
| Sta. Elena | VI | 11B | | | | | | | |
| Sta. Elena | VI | 13B | | | | | | | |
| La Marina | VI | 15B | | | | | | | |
| La Marina | VI | 16B | | | | | | | |
| La Marina | VI | 17B | | | | | | | |
| La Marina | VI | 18B | | | | | | | |
| La Marina | VI | 19B | | | | | | | |
| Cisne 1 | VII | 1B | | | | | | | |
| La Marina | VI | 20B | | | | | | | |
| La Marina | VI | 21B | | | | | | | |
| La Marina | VI | 22B | | | | | | | |
| La Marina | VI | 23B | | | | | | | |
| La Suiza | VII | 25B | | | | | | | |
| La Suiza | VII | 29B | | | | | | | |
| Cisne 1 | VII | 2B | | | | | | | |
| La Suiza | VII | 30B | | | | | | | |
| La Suiza | VII | 33B | | | | | | | |
| La Suiza | VII | 35B | | | | | | | |
| La Suiza | VII | 37B | | | | | | | |
| La Suiza | VII | 38B | | | | | | | |
| La Suiza | VII | 39B | | | | | | | |
| Cisne 1 | VII | 3B | | | | | | | |
| Antumapu | RM | 4.1 | | | | | | | |
| Antumapu | RM | 4.3 | | | | | | | |
| La Suiza | VII | 40B | | | | | | | |
| La Perla | VIII | 43a | | | | | | | |
| Cisne 2 | VII | 4B | | | | | | | |
| La Perla | VIII | 50a | | | | | | | |
| La Perla | VIII | 53a | | | | | | | |
| La Perla | VIII | 59a | | | | | | | |
| La Perla | VIII | 63a | | | | | | | |
| La Perla | VIII | 66a | | | | | | | |
| Cisne 1 | VII | 6B | | | | | | | |
| La Perla | VIII | 70a | | | | | | | |
| La Perla | VIII | 72a | | | | | | | |
| La Perla | VIII | 76a | | | | | | | |
| La Perla | VIII | 77a | | | | | | | |
| La Perla | VIII | 79a | | | | | | | |
| La Perla | VIII | 84a | | | | | | | |
| La Perla | VIII | 89a | | | | | | | |
| Requehua | VI | 8B | | | | | | | |
| La Perla | VIII | 90a | | | | | | | |
| La Perla | VIII | 91a | | | | | | | |
| La Perla | VIII | 92a | | | | | | | |
| Sta. Elena | VI | 9B | | | | | | | |
| Peñaflor | RM | A1 | | | | | | | |
| Peñaflor | RM | A3 | | | | | | | |
| Peñaflor | RM | A4 | | | | | | | |
| Peñaflor | RM | A6 | | | | | | | |
| Sn. Bernardo | RM | FR2A.1 | | | | | | | |
| Sn. Bernardo | RM | FR2A.2 | | | | | | | |
| Sn. Bernardo | RM | FR3H.1 | | | | | | | |
| Miraflores | RM | FR3H.2 | | | | | | | |
| Sn. Bernardo | RM | FR3H.3 | | | | | | | |
| Sn. Bernardo | RM | FRA2 | | | | | | | |
| Miraflores | RM | MPE.3 | | | | | | | |
| Miraflores | RM | MPE2 | | | | | | | |
| Miraflores | RM | MPE2.1 | | | | | | | |
| Miraflores | RM | MPH.1 | | | | | | | |
| Miraflores | RM | MPH.2 | | | | | | | |
| Miraflores | RM | MPR1.1 | | | | | | | |
| Miraflores | RM | MPR1.2 | | | | | | | |
| Miraflores | RM | MPR1.3 | | | | | | | |
| Miraflores | RM | MPR2.1 | | | | | | | |
| Miraflores | RM | MPRA.1 | | | | | | | |
| Teno | VII | Q1p | | | | | | | |
| Teno | VII | Q35 | | | | | | | |
| Teno | VII | Q35.2 | | | | | | | |
| Teno | VII | Q35.3 | | | | | | | |
| Cepario | Cepario | SAG | | | | | | | |
| Cepario | Cepario | SAG 62.4 | | | | | | | |

FIGURE 17

```
                         SEQUENCE LISTING


<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: PRIMER

<400> SEQUENCE: 1

agagtttgat cctggctcag                                                 20


<210> SEQ ID NO 2
<211> LENGTH: 19
<212> TYPE: DNA
<213> ORGANISM: Artificial Sequence
<220> FEATURE:
<223> OTHER INFORMATION: PRIMER

<400> SEQUENCE: 2

ggttaccttg ttacgactt                                                  19
```

BACTERICIDE COMPOSITION BASED ON A MIXTURE OF BACTERIOPHAGES FOR THE CONTROL OF BLACK PLAGUE IN PLANTS OR PARTS THEREOF, PREFERABLY THE WALNUT, CAUSED BY XANTHOMONAS ARBORICOLA PV. JUGLANDIS; PREPARATION METHOD AND APPLICATION

FIELD OF THE INVENTION

The present invention relates to a bactericidal composition based on bacteriophages for the control of the walnut blight in plants or parts thereof, preferably walnut; preparation method and application. The invention provides methods of isolation, propagation and application of bacteriophages against phytopathogens affecting trees/plants of commercial interest for their fruits, flowers or others, for prophylaxis, treatment or reduction of signs, in particular, for *Xanthomonas A*. pv *juglandis* in walnuts. The biological materials were deposited with the International Depository Authority PCM Polish Collection of Microorganisms, Institute of Immunology and Experimental Therapy, Polish Academy of Sciences, Ul. Weigle 12, 53-114 Wroclaw, Polonia, on Jun. 19, 2015 with Deposit Accession numbers PCM F/00087 to F/00093: Podoviridae family bacteriophage PCM F/00087 (ϴ4.1), PCM F/00088 (ϴ6), PCM F/00089 (ϴ36), PCM F/00090 (ϴM4-109a), PCM F/00092 (ϴM307-70a), PCM F/00091 (ϴM310-91a), and Siphoviridae family bacteriophage PCM F/00093 (ϴM2-2), under the provisions of the Budapest Treaty.

BACKGROUND

For producers of walnuts, and particularly for Chile—third Latin American producer, the presence of *Xanthomonas* pv *juglandis* (Xaj), the causative agent of the walnut blight of walnut (FIGS. 3A-3D) is a major problem. It is estimated that losses due to this disease, reach 50-80% in production (Chariot and Radix, 1993; Miller, 1934; Brandi et al, 2014.).

The diagnosis of AKI is currently delayed when significant renal damage has developed, making difficult to recover renal function, in part due to the current lack of tools for early diagnosis.

Walnut blight is one of the most important diseases, and is widely distributed in these crop areas (Loreti, 2001). *Xanthomonas* pv *juglandis* causes severe damage to leaves, branches, buds, petioles, rachis, catkins, fruits among other tissues, and is considered one of the main causes of performance decline in fruit and tree vigor (Belisario et al., 1999).

*X. arboricola* is a bacterial species associated with plants that includes strains responsible for the major diseases in stone fruit and nut strains. *X. arboricola* is divided into pathovars, some of which are classified as quarantine organisms. The three most economically important species in pathovars are pruni pathovars, corylina and *juglandis* responsible for bacterial spot of stone fruit trees, bacterial blight of hazelnut and walnut blight plague respectively. Recent studies have shown that pathovars pruni, corylina and *juglandis* are closely related phylogenetically (Fisecher et al., 2015).

Currently, the treatment available to control the walnut blight, consists mainly in agrochemicals based on copper. However, these agrochemicals have noticeably lost its effectiveness, and even require more than 5 applications to control outbreaks of the disease (manufacturers recommended dose).

Compounds based on copper in its different formulations such as agrochemicals, are the main tool used to control plant diseases. Despite its widespread use, its efficiency is increasingly challenged, especially due to the emergence of resistance in the phytopathogens microorganisms, and its important phytotoxicity.

This is how the effectiveness of treatment with copper-based products for control *X. arboricola* pv. *juglandis* has decreased over time, due to the selection and increase of bacteria resistant to these agrochemicals, since bacteria have generated or acquired different resistance mechanisms.

This situation gets worse, by considering the evidence from different scientific studies that suggest the transfer of copper resistance genes between bacteria. On the other hand, the excessive use of copper compounds in the field has severe repercussions since this metal accumulates on the floor in highly toxic waste for crops and the environment. In Chile, the control of the walnut blight, is based on applications of copper products, which in a season can reach even up to 10 or more applications, depending on location, weather conditions and inoculum pressure. This situation is explained by the number and poor application techniques, which have selected strains resistant to copper.

In fact, in 2007, the first local study was conducted (only Maule and Metropolitan regions), where the presence of *X. arboricola* pv *juglandis* resistant to $Cu^{+2}$ was determined (Esterio et al. 2007). Resistance levels fluctuated between 8 and 64 μg/mL and a direct relation and close dependence between resistance level and copper selection pressure were established.

Current results (in review), of the same inventors than the present bactericide composition have established the presence of *X. arboricola* pv. *juglandis* in all sampled orchards of the four main nut producing regions in Chile (VI, VII, VIII and XIII). Furthermore, it has been found that more than 76% of all Xaj isolates are resistant to concentrations higher than 16 μg/mL of $Cu^{+2}$ (FIG. 1).

This demonstrates that current management methods with compounds based on copper, do not reach and effective control, causing the prevalence of this disease in most of the national walnut orchards. The situation described above also applies to other plants such as stone fruit and not just the walnut, where the combat, control or management of infection due to *Xanthomonas arboricola* pv *juglandis* presents the same difficulties.

Arises, the need to develop more effective alternatives without phytotoxic risk and low environmental impact for the treatment of the walnut blight. As a solution, the present invention suggests a bactericidal composition based on a mixture of bacteriophages (phage), which is able to infect and kill specifically *X. arboricola* pv. *juglandis*, generating a control and effective protection to plants or parts thereof, including trees selected from the group consisting of walnuts and pits, and preferably, walnuts, against the walnut blight.

The major advantages of using a mixture of phages as a bactericide that may be mentioned are: its high specificity, its safety, its high rate of replication, the fast development of new formulations, and the fact of being a natural product.

Specifically, in the agricultural field, additional advantages are: the unrestricted use, nor of entrance to orchard, neither of deficiencies, and it is feasible to use with cupric treatments. In addition, it supports organic farming and integrated production.

Thus, the main objective of the present invention is a bactericidal composition based on bacteriophages to control the walnut blight or infection *Xanthomonas arboricola* pv *juglandis*, in plants or parts thereof, including trees selected from the group consisting of walnuts and pits, and preferably walnuts.

It is yet another objective of the present invention, methods of isolation, propagation and application of bacteriophage against *Xanthomonas* pv *juglandis*, for prevention, treatment or reduction of signs due to *Xanthomonas* pv *juglandis* on plants or parts thereof, including trees selected from the group consisting of walnuts and pits, and preferably walnuts. The composition is stabilized in a solution that allows the viability and bactericidal activity of phages, and thus favors the application thereof in the field.

BRIEF DESCRIPTION OF THE FIGURES

FIG. 17: host range to the seven selected phages. Green boxes indicate no bacterial growth, little orange boxes indicate bacterial growth, yellow boxes indicate high bacterial growth, gray boxes indicate full bacterial growth.

DETAILED DESCRIPTION OF THE INVENTION

The present invention proposes a bactericidal composition based on bacteriophages, which is able to infect and kill specifically *Xanthomonas arboricola* pv *juglandis* (Xaj). The present invention also provides methods of isolation, propagation and application of bacteriophages against phytopathogens affecting trees/plants that are of commercial interest for their fruit, flowers etc., or others, for prevention, treatment or reduction of signs, in particular, for *Xanthomonas A*. pv *juglandis* in walnuts.

Some advantages of the present composition are the following: its high specificity, its safety, its high rate of replication, the fast development of new formulations, and the fact of being a natural product. Additionally, and is compatible with the use of copper. Table 1 briefly summarizes the advantages of the composition of the present invention based on the bactericidal copper compounds

TABLE 1

Main differences between use of bacteriophages and copper-based agrochemicals such as treatment plants.

| Present composition | Agrochemical (Cu) |
|---|---|
| Specific | Non specific |
| Safe | Toxic |
| Autoreplicable | Dilutable |
| Natural product | Chemical product |
| Without restrictions of use | Restricted use (phytotoxic) |

Specifically, in the agricultural field, additional advantages are: the unrestricted use, nor of entrance to orchard, neither of deficiencies, and it is feasible to use with cupric treatments. In addition, it supports organic farming and integrated production.

Thus, the main objective of the present invention is a bactericidal composition based on bacteriophages to control the walnut blight in plants, especially walnuts.

It is yet another objective of the present invention the methods of isolation, propagation and application of bacteriophage against *Xanthomonas* pv *juglandis*, for prevention, treatment or reduction of signs due to *Xanthomonas* pv *juglandis* on walnuts. The composition is stabilized in a solution that allows the viability and bactericidal activity of phages, and thus favors the application thereof in the field.

Figure 16:
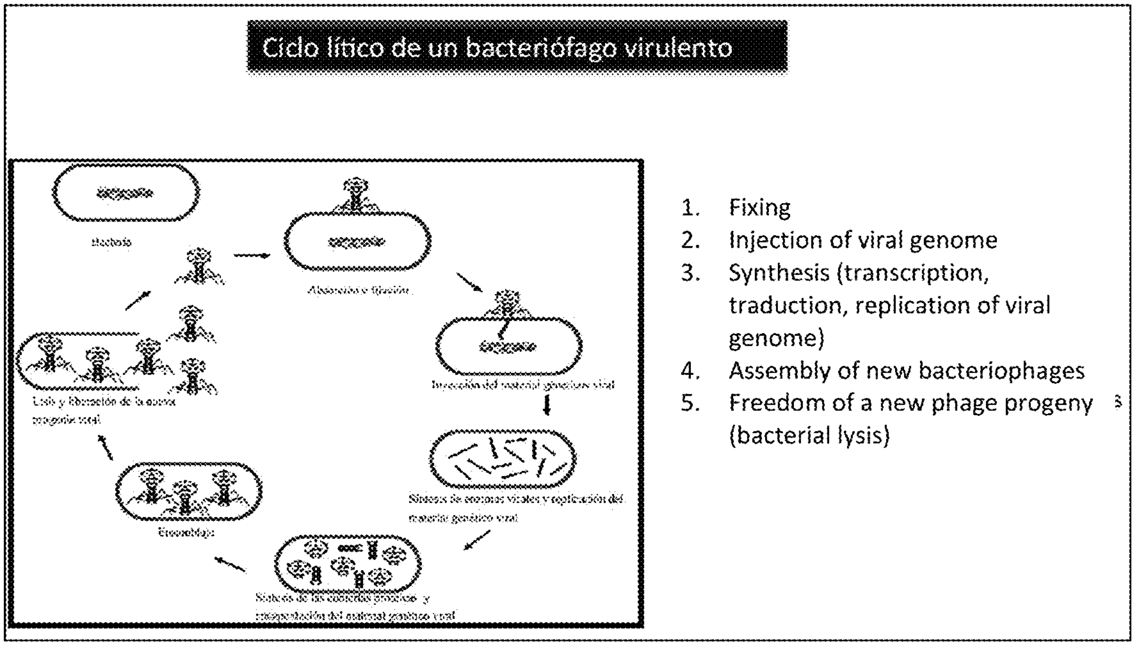
FIG. 16: Shows the lytic cycle of a virulent bacteriophage comprising: 1) fixation, 2) injection of the viral genome, 3) synthesis (transcription, translation, viral genome replication), 4) Assembly of new bacteriophages, and 5) release of new phage progeny (bacterial lysis).

Bacteriophages are viruses that infect only bacteria, and thus are harmless to eukaryotic host cells (walnut, human, etc.). It is estimated that bacteriophages are the most abundant biological entity on the planet with a ratio of 10 phage per bacterium. There are lytic bacteriophages that, after infecting and multiplying themselves in their host bacteria, destroy it (bacterial lysis), releasing a new progeny bacteriophage, which is composed by hundreds of viral particles ready to infect more bacteria (specific host) repeating the lytic cycle (FIG. 16). Thus, the pathogenic bacteria is controlled, without affecting the beneficial microbiota of trees nor leaving residues in the environment.

Results

The present composition comprises a mixture of phages is able to infect and kill, *Xanthomonas A*. pv *juglandis*, even resistant to current treatments ($Cu^{+2}$) (FIGS. 2A and 2B) strains. Specifically, the present bactericidal composition in one embodiment thereof, comprises seven highly lytic bacteriophages, characterized in atingentes their properties as bactericides. These bacteriophages are ⊖4.17 (deposit number PCM F/00087), ⊖6 (deposit number PCM 00088), ⊖36 (deposit number PCM 00089), ⊖M4-109a (deposit number PCM 00090), BM3 ⊖7-70 (deposit number PCM 00092), 9M310-91a (deposit number PCM 00091), and ⊖M2-2 (deposit number PCM 00093). The restriction pattern of the genomes of the phages is a quick and easy tool to differentiate and identify each bacteriophage, this is shown for each of the phages in FIG. 5. Moreover, the seven bacteriophages were resistant to action of copper. The main features of these phages are shown in Table 2.

TABLE 2

Main characteristics and classification of selected bacteriophages

| Phage | Digestion | Genome Size (pb) | Membrane | Phage type | Inactivation copper | RFLP Group |
|---|---|---|---|---|---|---|
| Θ6 | DNA | 42288 | Absence | Podovirus | No | B |
| Θ36 | DNA | 40834 | Absence | Podovirus | No | A |
| Θ 4.1 | DNA | ND | Absence | Podovirus | No | A |
| ΘM4-109a | DNA | 39087 | Absence | Podovirus | No | A |
| ΘM2-2 | DNA | 38075 | Absence | Sifovirus | No | C |
| ΘM307-70a | DNA | 40302 | Absence | Podovirus | No | D |
| ΘM310-91a | DNA | ND | Absence | Podovirus | No | B |

An important criterion for selecting bacteriophages agronomic application is having very low resistance in bacteria that infect. Thus, one can remove almost all of the pathogen, and the combination of them ensures a very low probability that generate resistance to the composition. The percent resistance for each selected bacteriophage was determined in their host strain and tabulated in Table 3.

TABLE 3

Determination of resistance percentage and information isolation Bacteriophages

| Phage | % resistance | Xaj Host | Type of sample of isolation | Place of origin (region) |
|---|---|---|---|---|
| Q4.1 | 0.02 | Q4.1 | water | Peñaflor (XIII) |
| Q6 | 0.00 | 6 | water | Lonquén (XIII) |
| Q36 | 12.00 | 36 | water | Lonquén (XIII) |
| QM4-109a | 0.09 | 109a | soil | Amalia (VII) |
| QM307-70a | 0.00 | 70a | water | Porfirio (VIII) |
| QM31-91a | 0.03 | 91a | water | La Perla (VIII) |
| QM2-2 | 12.00 | 31 | water | Guitro (VI) |

Figure 1:
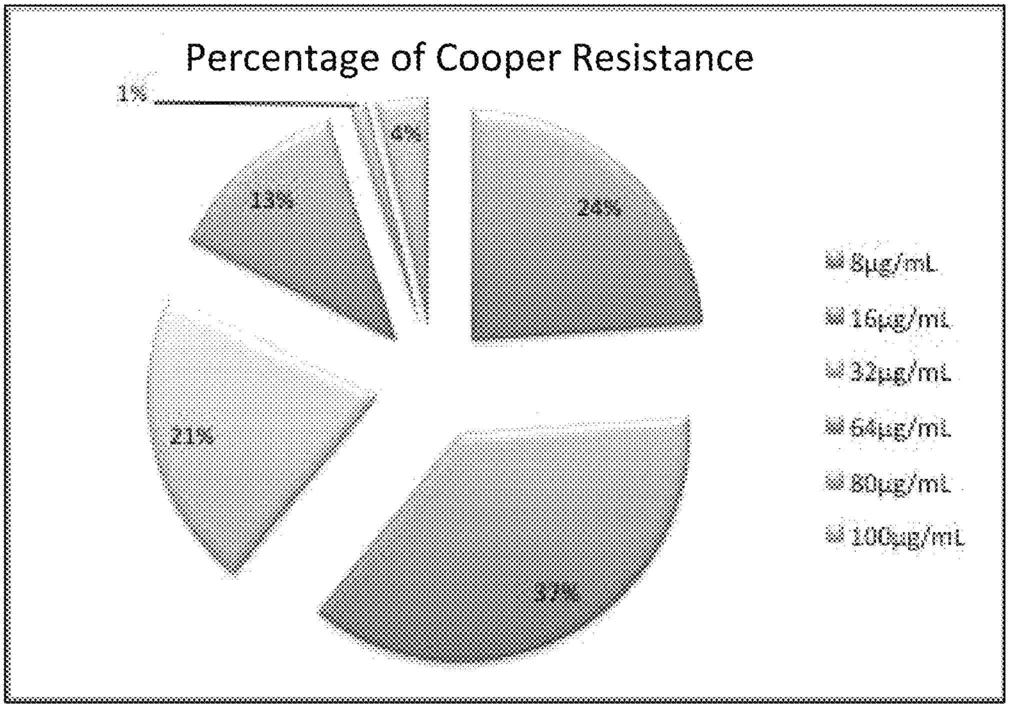
FIG. 1: Shows the percentage distribution *Xanthomonas A*. pv *juglandis* isolates resistant to different concentrations of copper sulfate.
Figure 2A:
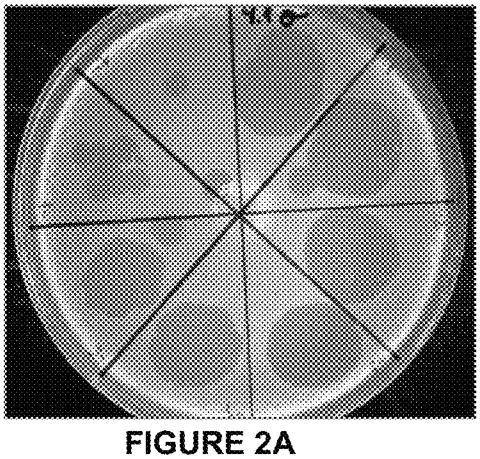
FIGS. 2A and 2B: A: Shows lysis plates of bacteriophage ⊖4.1. B: Strain of 4.1 and 830 cultures of *Xanthomonas A*. pv *juglandis* in phages presence Phages are capable of lysing completely bacterial cultures.
Figure 2B:
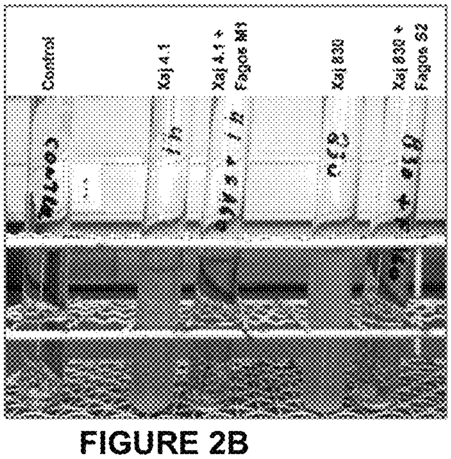
Figures 3A, 3B, 3C, 3D:
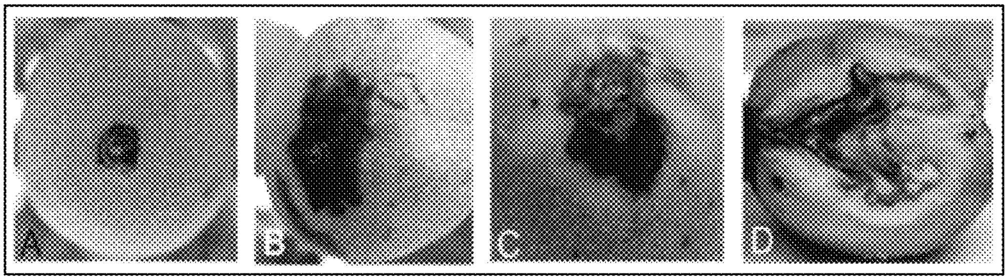
FIGS. 3A-3D: Displays fruits of walnut trees affected by walnut blight (*Xanthomonas* pv. *juglandis*).

The lytic capacity was tested in vitro, on cultures of various *Xanthomonas* pv *juglandis* in solid and liquid media. Phages are able to completely lyse liquid cultures of the pathogenic bacteria, and generate solid media plates completely transparent lysis (FIGS. 2A and 2B). This bactericidal composition in one of its embodiments comprises 7 bacteriophages, which have a bactericidal action over 90% of the 87 tested strains *X. arboricola* pv *juglandis* (Table 3), of which more than 76% of the bacterial strains are resistant to different concentrations of copper. These strains were isolated from different cultures from walnut nut main regions (regions VI, VII, VIII and XIII). This property of the present composition ensures a high probability of disease control in different locations (Nocedales). Table 4 summarizes the host range of bacteriophages 7 above, and the detail of each of them can be seen in FIG. 17.

TABLE 4

Summary of host range of 7 bacteriophages selected, tested with various strains of *X. arboricola* pv *juglandis* isolated from the main producing regions of nuts. The table shows the distribution of the different isolates tested Xaj and percentage of coverage bactericidal composition shown phages.

| | Group of Xaj infected by phages | | Group of Xaj did not infected by phages | |
|---|---|---|---|---|
| RM | 17 | 4 | 5 | 1 |
| VI | 12 | 3 | 1 | 1 |
| VII | 18 | 4 | 1 | 1 |
| VII | 29 | 3 | 0 | 0 |
| Culture Collection | 4 | ND | 0 | 0 |
| Total | 80 | 14 | 7 | 3 |
| Percentage of bactericide coverage | | | | 91.95% |
| Percentage without bactericide coverage | | | | 8.05% |

Figure 9:
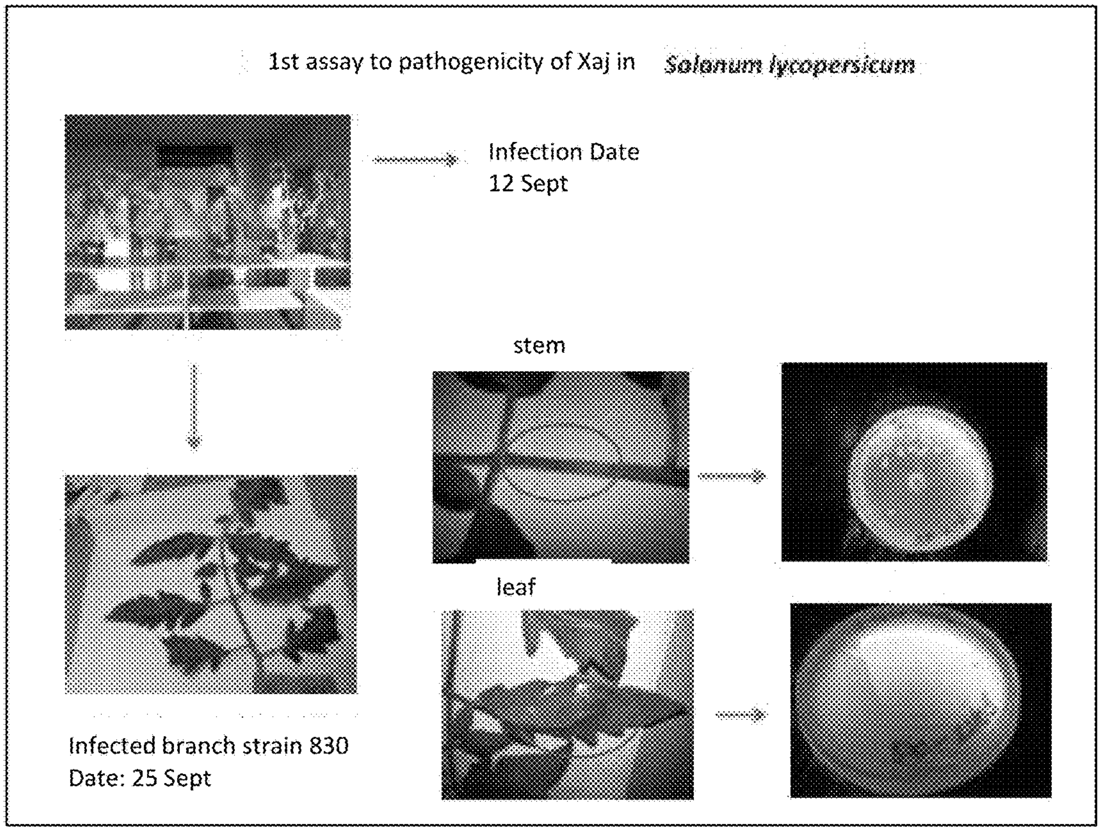
FIG. 9: Shows testing methodology of Xaj pathogenicity in tomato (*Solanum lycopersicum*).
Figure 10:
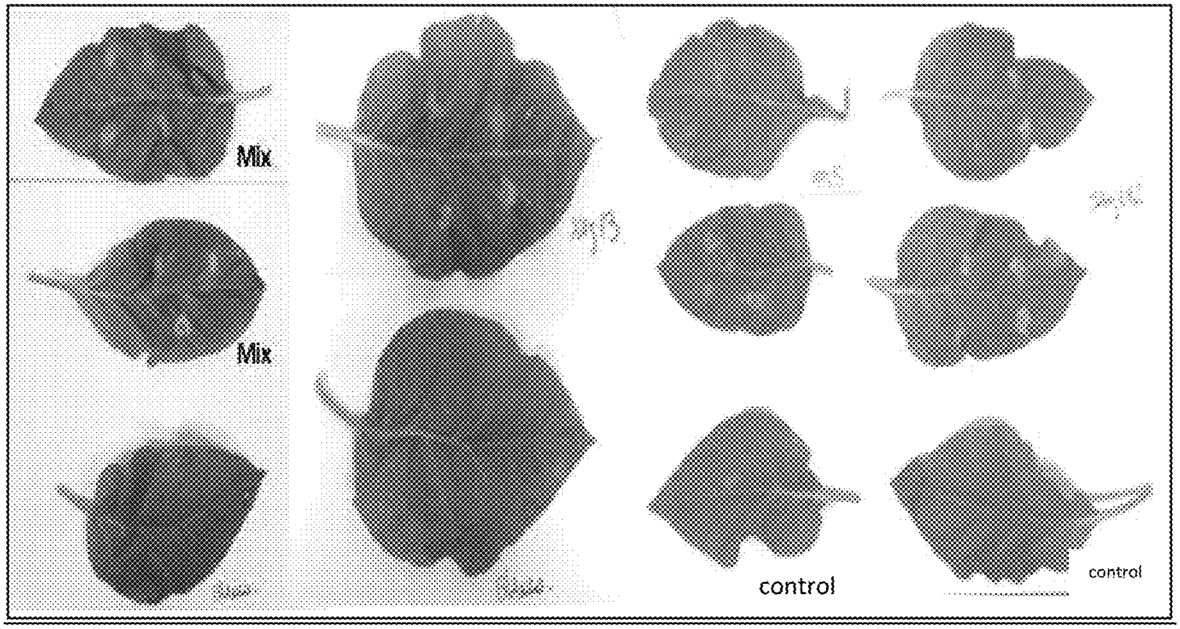
FIG. 10: Shows test result of Xaj pathogenicity in snuff tree (*Nicotiana tabacum*)

Xaj strains that were virulent were chosen to determine this feature models and snuff tomatoes plants was used. In tomato surface it eroded leaves and branches, and bacteria (See FIG. 9) was added. To snuff they leave with individual strains Xaj and mixtures thereof infiltrated (See FIG. 10). More virulent strains Xaj were chosen for evaluation tests with phages protection. To assess the ability to control Xaj with bacteriophages were performed using immature fruits of walnut (walnut), walnut leaves and leaves snuff. The results indicated that the groups of untreated fruits with bacteriophages, developed similar to the walnut blight, brown-black coloration signology in inoculation area and internal necrotic (mesocarp) tissue, together with the recovery of the strain Xaj inoculated. However, the groups treated with bacteriophage some had lower degree of signology walnut blight, although generally the presence of Xaj inoculated only in isolated cases and in low concentration was detected. Similar results were observed in trials with leaves, in the treated groups blackening was observed in puncture sites and the presence of pathogenic bacteria in the area of infection, unlike the groups treated with some of the bacteriophages of the present invention. All of the above according to detail provided in the Examples section.

Therefore, the results showed that the groups not treated with bacteriophage generated small black spots in the puncture site, necrotic endocarp tissue and the presence of bacteria in the area of infection, unlike the groups treated with the bacteriophages of the present invention. Thus, the present invention comprises native bacteriophages (bactericides) useful for conducting a treatment for *Xanthomonas* pv *juglandis* control, the causative agent of the walnut blight. In the present composition it is stabilized said mixture in a solution that allows the "viability" and bactericidal activity of phages, so, to favor its field application.

Finally, different media formulations who managed to stabilize bacteriophage in time and can be field applied safely and that these not Formulating the composition of antibacterial inactivate is a concentrated form comprising in one of its embodiments, is evaluated seven bacteriophages equivalent amounts of them ($10^9$ PFU/mL). Antibacterial composition further comprises a buffer solution and/or stabilizing agents bacteriophages be so busy crops with safety to maintain bactericidal activity. The buffer solution basically comprise one or more of the following components: NaCl, $MgSO_4$, Tris-HCl, gelatin, pH 7.5. As stabilizing agents may be used salts which maintains osmotic pressure and useful as cofactor phage absorption, among others. Furthermore, the antibacterial composition to has a high stability at a temperature range between 4° to 45° C.

EXAMPLES

The following examples are included and detailed to demonstrate the features of the present invention.

Example 1

Means, isolation, and crops conditions for *Xanthomonas arboricola* pv *jualandis* strains For proper isolation of bacteriophages, it is first necessary to isolate the host bacteria. It is important to mention that "host bacteria or "host" refer to the bacteria that phages are able to infect, reproduce and lyse (kill).

Figure 4:
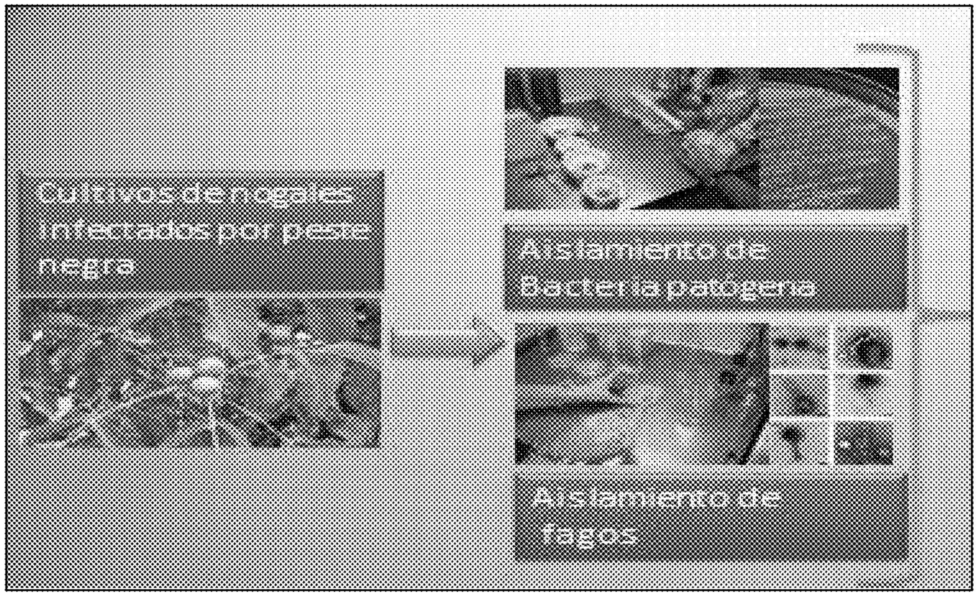
FIG. 4: Shows a diagram of phages selection method of the present composition.

To isolate Xaj, samples of leaves, fruits, and buds of walnuts with symptoms of walnut blight were collected, coming from the main nuts producer's regions of Chile (VI, VII, VIII and XIII) (FIG. 4).

The samples were processed using the method described by Moragrega et al. (2012). To obtain isolates of *Xanthomonas arboricola* pv *juglandis*, a segment of 1 $cm^2$ of infected tissue was macerated into 300 μL of physiological buffered water (buffer AFT) (0.14 M NaCl, 2.6 mM $NaH_2PO_4.2H_2O$ and 7.5 mM $Na_2HPO_4$.X $12H_2O$). Some isolates were performed from the homogenized into solid medium B. King. (2% Protease Peptone, 0.15% $KaPO_4$, 0.15% $MgSO_2$× $7H_2O$, 1% glycerol and 1.5% agar. PH 6.5-7.0). The plates were incubated at 28 C for a period of 72 to 120 hours.

Isolated colonies that showed the classic morphology Xaj (yellow colonies, translucent, viscous and with smooth edges) were selected and identified through amplification and subsequent sequencing of a 16S ribosomal gene segment. Basically, the 16S ribosomal gene of the isolates was amplified using universal primers SEQ ID No. [27F (5'-AGAGTTTGATCCTGGCTCAG-3')] and SEQ ID No. 2 [1492R (5'-GGTTACCTTGTTACGACTT-3')](Weisburg et al, 1991). FCR conditions used were described by Trabal et al. (2012).

The amplificons of 16s ribosomal gene were digested by the enzyme Alu I and run into electrophoresis in polyacrylamide gel at 7.5%. This generates a pattern of characteristic fragments for Xaj, which was subsequently used for quick identification of these strains.

It was possible to obtain a strain collection of 87 *Xanthomonas arboricola* pv *juglandis*, characterized according to its level of resistance to copper. The Xaj were preserved by cryopreservation in glycerol 50% v/v, frozen at −80 C, until its further use.

Getting Bacteriophages

Example 2

Sample Processing, Isolation and Purification of Bacteriophages

Samples of soils under walnut trees and irrigation water from different farms were collected. To process the soil samples, a volume of SM buffer (NaCl 5.78 g; $MgSO_4$ $7H_2O$ 2 g; Tris 6.057 g gelatin 0.1 g for one liter of water) was added to the sample, according to its weight, homogenized and stirred for all night, then centrifuged at 6000 g for 15 minutes and filtered through 0.2 micron filter pore. To process water sample, it centrifuged at 6500 g for 15 minutes and filtered through 0.2 micron pore filter 10 mL of nutritious medium (beef extract 3 g, peptone 5 g for one liter of distilled water) and 10 mL of samples were added to both filtrates (water and ground SM buffer). Each one was inoculated with 100 uL of cultures from 5 different strains Xaj. It was incubated at 28° C. and stirred for 48 hours. Later, it was centrifuged at 6500 g for 15 minutes and the supernatant was filtered through 0.2 micron pore filter. When the bacteria grow in the culture medium any phage present which can infect her will proliferate altogether.

Phage detection was performed by lysis plaques (double agar method). The phages in suspension are subsequently detected by their ability to lyse bacteria and prevent their growth (FIG. 2A). Thus, when phages are placed on a bacterial lawn of *X. arboricola* pv *juglandis* in a solid culture medium, clear circles are observed, called lysis plaques (PFU) or inhibition halo, generated by the multiplication of the phages from a viral particle, which reach more host bacteria preventing their growth.

For isolation and classification of phages of *Xanthomonas arboricola* pv *juglandis*, a plate lysis was generated, well separated from others (single phage), assuming that is was initiated by the same viral particle, so that all phages originated from this suspension come from the same viral particle and are practically identical (clone). To insure clonality the procedure was repeated three times.

In order to avoid the presence of non-virulent temperate phages, transparent lysis plates without bacterial growth inside will be selected, since it may be due to lysogenized bacteria Preparation of phage stocks and conservation of phage collection. Phages were reproduced on plates with solid base nutritious (NB) medium, and the host bacteria mixed with soft agar NB (0.7% agar) spread on the surface. After the soft agar turned into gel, 10 drops of 20 uL were added, and it was incubated at 28 C for 24-48 hours. Once bacteria lysis was observed due to infection of the phage, 20 ml_of SM buffer was added in the plates and stirred for 6 hours. SM buffer containing phages was collected, to be centrifuged and filtered (0.2 micron). These phage suspensions were stored at 4° C. and at −70 C with 50% glycerol or directly. This method generates phage stocks with concentrations between $10^{10}$-$10^{11}$ PFU/mL.

Figure 7:
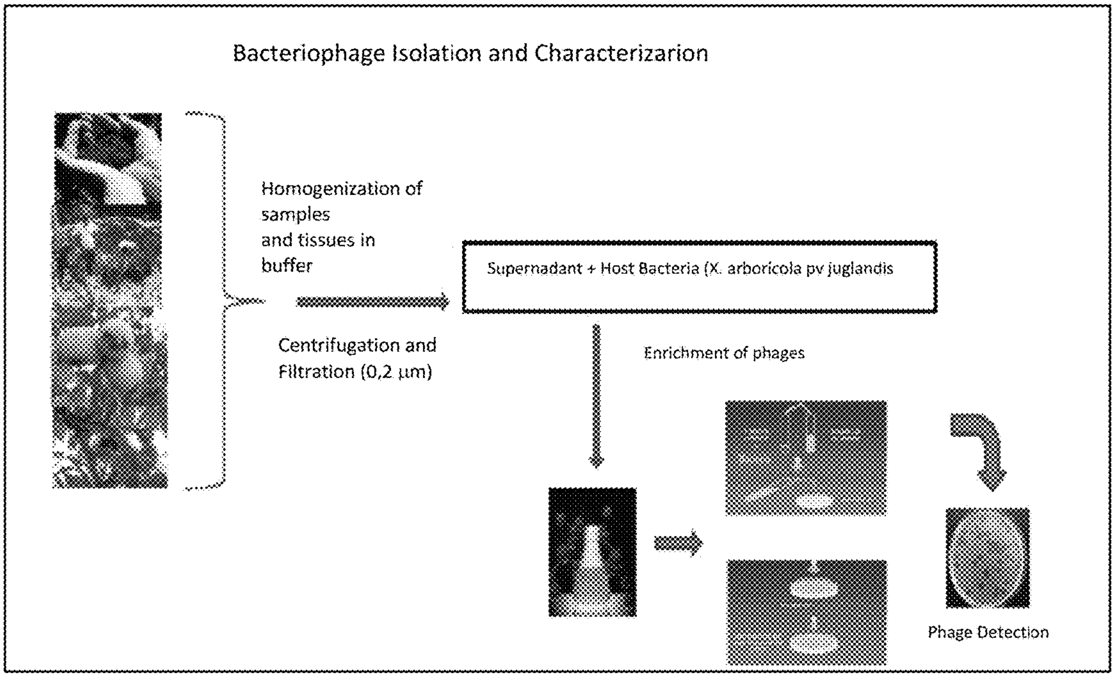
FIG. 7: Scheme of bacteriophage isolation methodology used prior to their characterization, with screening purposes for the mixture of the present composition

One phage collection of seven bacteriophages ⊖4.1 (deposit number PCM F/00087), ⊖6 (deposit number PCM F/00088), ⊖36 (deposit number PCM F/00089), ⊖M4-109a (deposit number PCM F/00090), ⊖M307-70a (deposit number PCM F/00092), ⊖M310-91a (deposit number PCM F/00091), and ⊖M2-2 (deposit number PCM F/00092) was obtained. The outline of this method is shown in FIG. 7.

Example 3

General Characterization of Bacteriophages

The general characterization of the selected phages was performed. An important component of the strategy of using phage as a bactericide, is the use of phage mixtures that have different infection routes, to reduce the frequency of bacteria phage resistant strains. Phages with many differences have usually different infection routes.

Determination of the size and nature of nucleic acids: nucleic acids from bacteriophages was extracted and purified, for perform enzymatic tests with deoxyribonuclease and ribonuclease, determining the genome type of bacteriophage. The size of the molecules will be estimated by agarose gel electrophoresis 0.4%, using high molecular weight standard. Seven bacteriophages were found to have DNA genomes and their sizes are shown in Table 2.

Presence of membrane. This was checked by sensitivity to organic solvent (chloroform 1% v/v). These agents affect the phages causing deficiency in infection and therefore a decrease in their titles, A sensitive phage will be considered, ie with membrane, when its title decreases at least three orders of magnitude. None of the bacteriophages presents membrane (Table 2).

Morphological structure. The size and shape of each bacteriophage was determined through transmission electron microscopy. For this, the phages were purified and concentrated by CsCl concentration gradients, and then photographed (FIG. 6).

Example 4

Restriction of Fragment Length Profiles (RFLP)

Figure 8:
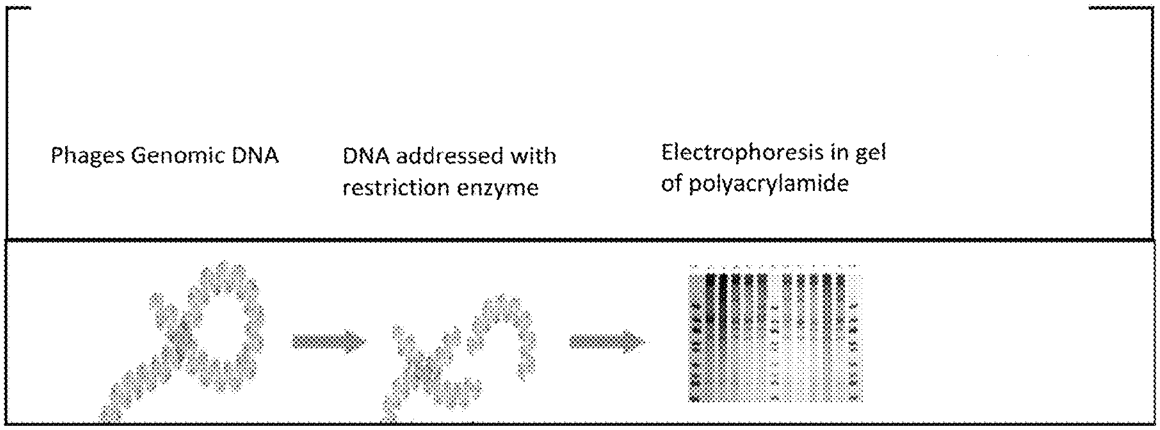
FIG. 8: Scheme of genomic characterization methodology of bacteriophages used prior to the selection of the phages mixture of the present composition (RFLP).

For the differentiation of bacteriophages, a digestion of the seven phage genomes, with the enzyme TaqI was performed, according to j manufacturer's recommendations, for 3 hours. Followed by a polyacrylamide gel electrophoresis (7.5%) for 2 hours at 100 volts (FIG. 8).

Figure 5:
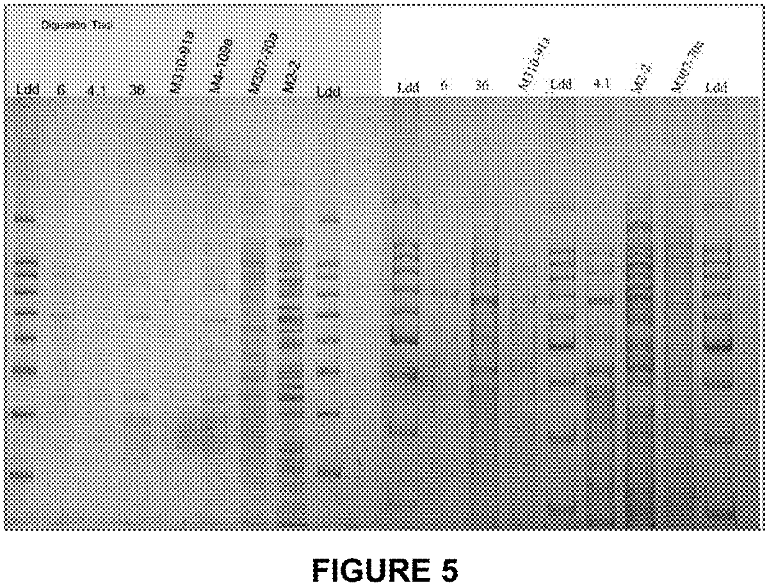
FIG. 5: Digestion pattern of seven selected phage genomes. It was performed with the enzyme TaqI and 100 volts electrophoresed for one hour.
Figures 6A, 6B:
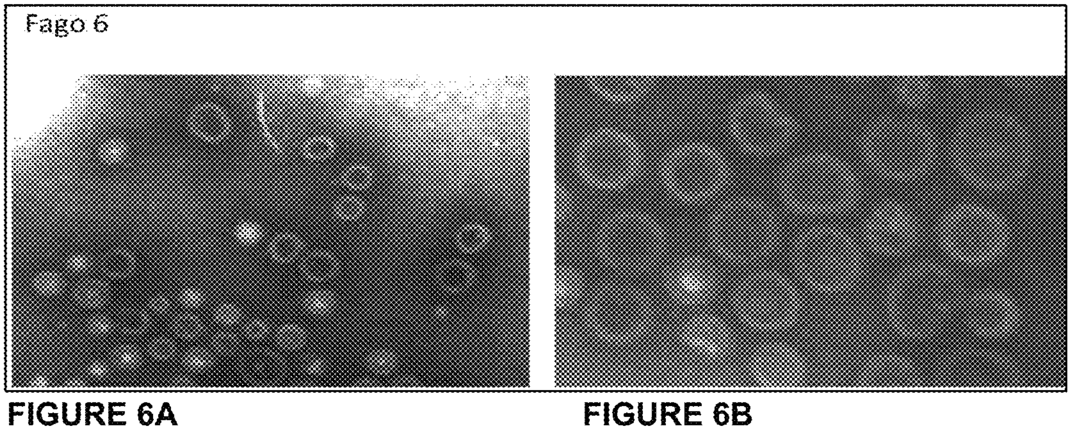
FIGS. 6A-6L: Electron microscopy of the seven bacteriophages from the patent. Shows morphology of each of the bacteriophages.
Figures 6C, 6D:
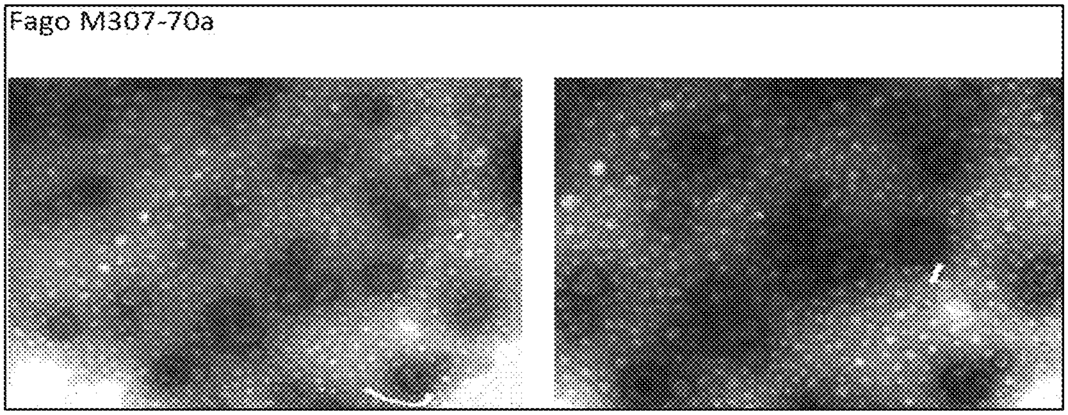
Figures 6E, 6F:
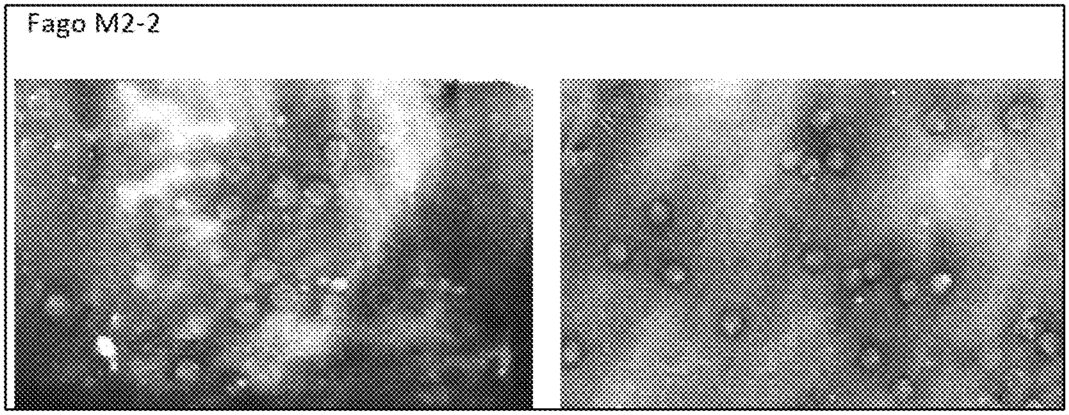
Figures 6G, 6H:
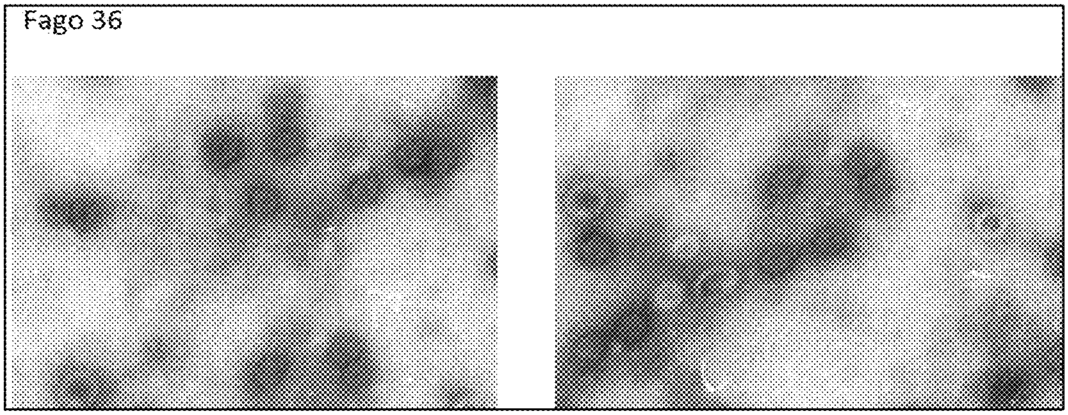
Figures 6I, 6J:
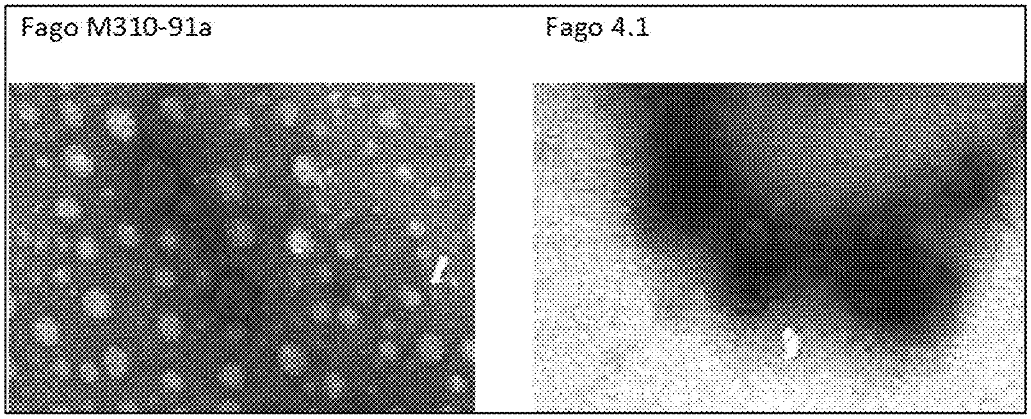
Figures 6K, 6L:
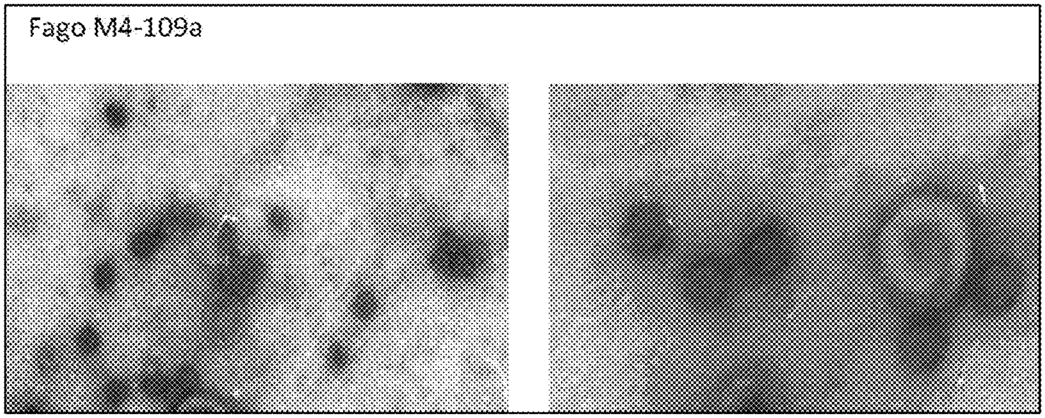

Bacteriophages were grouped into four restriction profiles, which included: Group A: ⊖36, 9M4-109a and ⊖4.1 (deposit number PCM F/00087); group B: ⊖6 and ⊖M310-91a; group C: ⊖M2-2; and group D: ⊖M307-70a. This is useful in both measurements of its presence as well as in the protection actions, since the genetic profile can be used as a fingerprint (FIG. 5).

Example 5

Determination of Phage Host Range Against *Xanthomonas arboricola* pv *jualandis*

Infection specificity of the seven individually selected phage was analyzed through the double agar method. This test was performed including all the strains of the obtained strain collection (87 isolates) in the step mentioned above. Three micro drops with concentrated phage were added on a lawn of different *X. arboricola* pv *juglandis* phage strains in order to test. The results obtained were presented as: lysis plates with clear zone, plates with cloudy area, or without growth inhibition (FIG. 17). The information was tabulated in order to identify the phages with lytic effect over the greatest number of strains.

The percentage of bactericidal coverage (host range) among the 87 strains Xaj was 91.95%.

Example 6

Determination of Resistance the frequency of resistant bacteria was measured by counting the number of colony forming units (CFU) persisting in the phage presence (after infection). Serial dilutions from a bacterial culture in exponential growth were performed and were infected with a high multiplicity of infection (MOI) of phage. In parallel, uninfected controls were performed. The ratio between the number of CFU of the infected dilutions versus controls uninfected was considered resistant frequency.

The seven phages had the following percentages of phage resistance: Θ6 and ΘM307-70a an 0%; Θ4.1 an 0.02%; ΘM310-91a an 0.03%; ΘM4-109a 0.09%; and phage Θ36 and ΘM2-2 12%. There was no resistance to the mixture of the seven bacteriophages.

Example 7

Evaluation of Phage Effectiveness on Xaj Infection Control.

a. Determination of Phage Protection Against Xaj in Fruits and Leaves (Individual Bacteriophages)

Figure 12:
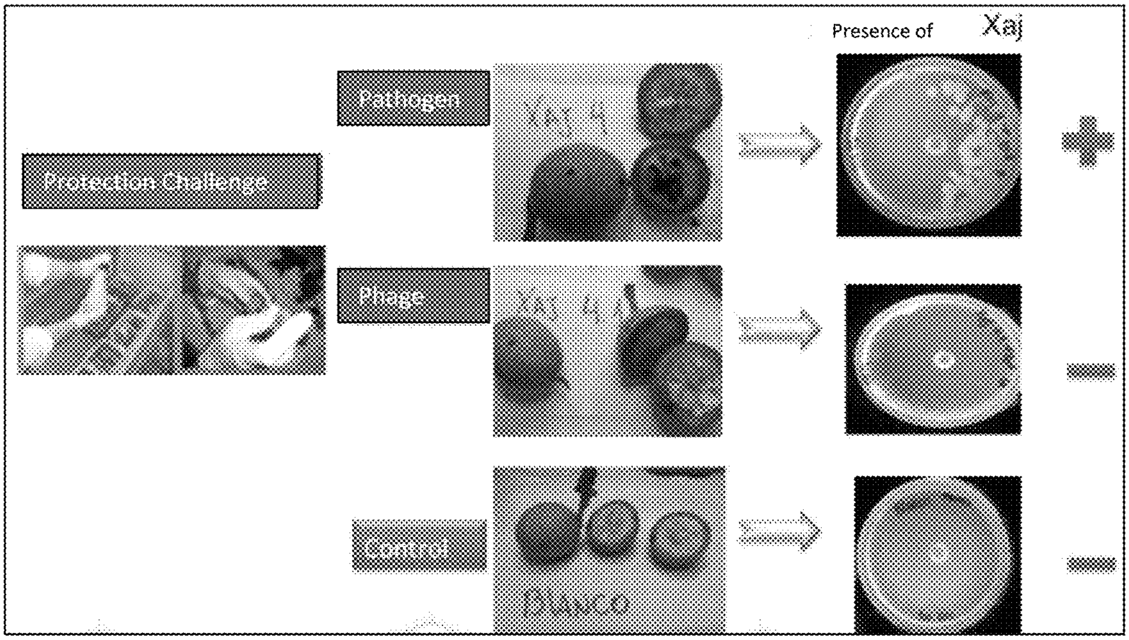
FIG. 12: Scheme for evaluating efficacy of phages in controlling Xaj, in unripe walnut fruits.

It consisted mainly in an artificial inoculation of the bacteria *X.* pv *arboricola. juglandis* on immature and asymptomatic walnut fruits and free of walnut blight, which were used to evaluate the bactericidal activity of bacteriophages. It was held under controlled environmental laboratory conditions as described below (FIG. 12):

Immature fruits of nuts and leaves asymptomatic with walnut blight, were collected to be used in in vivo inoculation trials of bacteriophages against *X. arboricola* pv *juglandis.*

Figure 11:
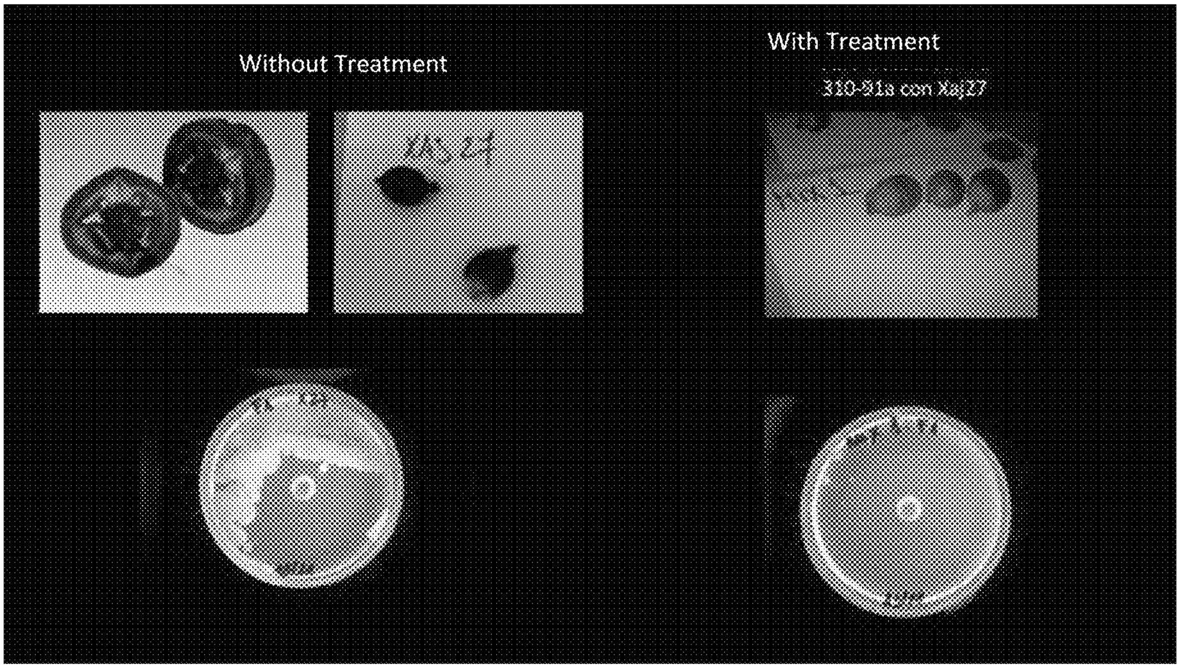
FIG. 11: Result of effectiveness of phages in controlling Xaj in unripe walnut fruits evaluation. It shows untreated group and treatment of a phage.

The fruit and leaves were disinfected by immersion in sodium hypochlorite at 5% and subsequently washed with sterile distilled water and dried at room temperature, before being infiltrated with bacteriophages ($10^9$ PFU/mL) selected through injection, in the equatorial j zone of the fruits and on the leaves (in triplicate), and in turn inoculated with *X. arboricola* pv *juglandis* ($10^8$ CFU/mL) in the demarcated areas for protection. As positive infection and safety controls, fruits were inoculated with only pathogenic bacteria and bacteriophages. The fruits were incubated at 25° C. in sterile boxes, at a relative humidity of 90%, with photoperiods of 16 hours of light, for 15 days. Incidence and severity (progression) of the infection in inoculated fruits was evaluated through a cross-section. The incidence of infection was determined by the presence of necrosis signs around the inoculation site and the presence of *X. arboricola* pv *juglandis* in the fruit. The severity was determined by the percentage of necrosis generated in the fruit due to the infection. Results were compared between groups of treated fruits with bacteriophages and untreated ones he results indicated that the group of fruits infected with the strain of Xaj 27 and the use of only one phage (⊖M310-91a), presented a light brown color only in the area of infection, and no bacteria presence was detected in fruits. However, non-treated group with bacteriophage ⊖M310-91a, presented blackening and necrotic tissue in over 75% of the fruit. In all cases, the pathogenic bacteria was recovered from infection (FIG. 11). A similar result was obtained when the phage ⊖4.1 (FIG. 12) was used.

Figure 13A:
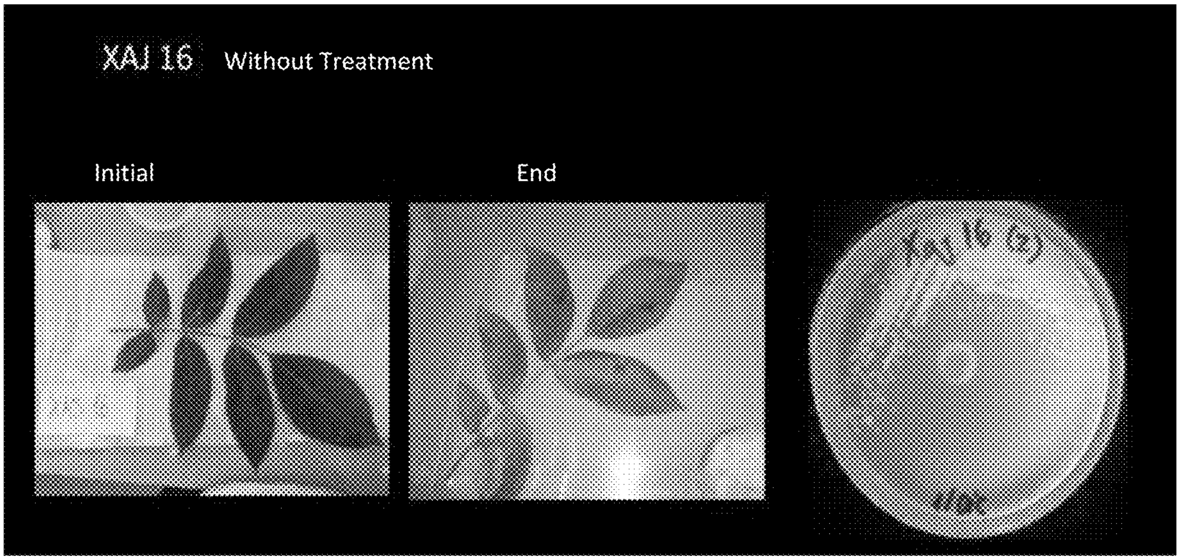
FIG. 13: Result effectiveness of phages in controlling Xaj in walnut leaves evaluation. Disease signs and re-isolation of the bacteria (laceration sheet method) are shown. A: Group Only with Xaj; B: Group treated with phage; C Medium control safety.
Figure 13B:
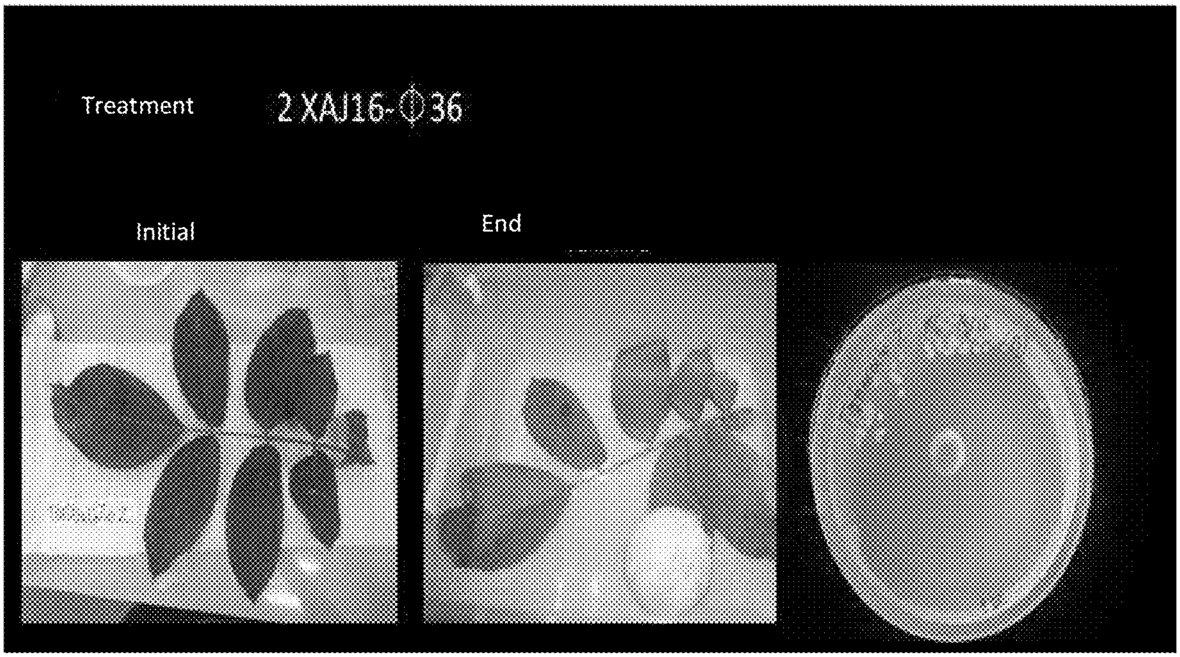
Figure 13C:
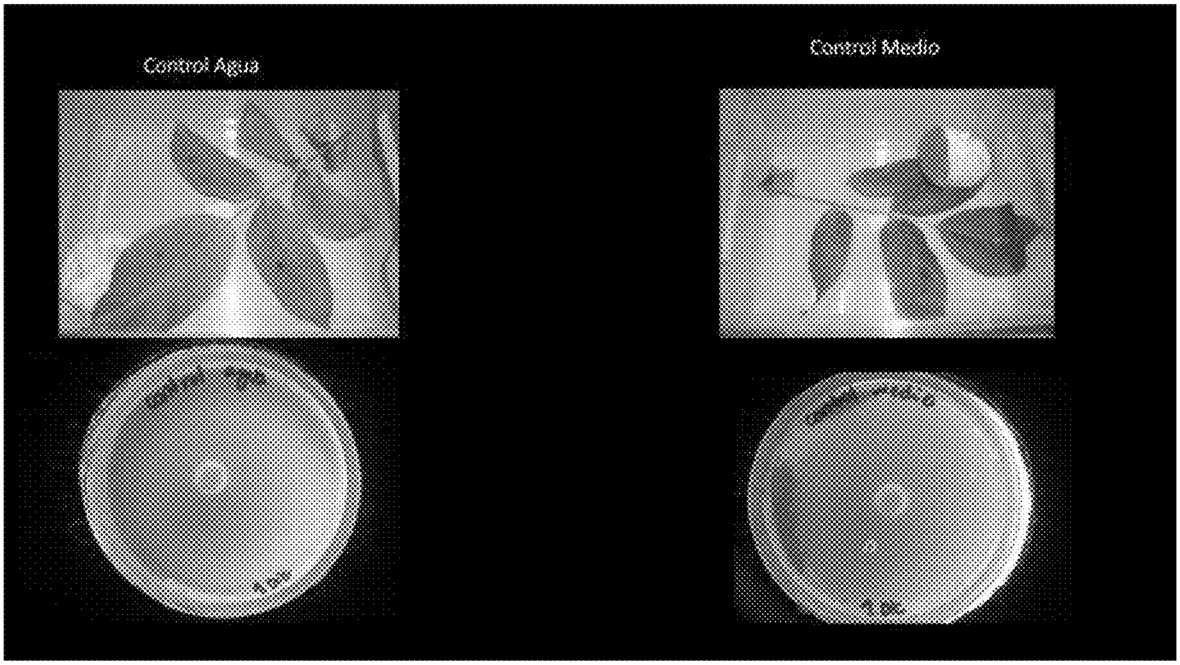

For leaves the incidence and severity (progression) of infection was evaluated by the presence of necrosis signs surrounding area of inoculation and of *X. arboricola* pv *juglandis* presence. The severity was determined by the advance distance generated from the injection point. Results were compared between groups of leaves treated with bacteriophage and untreated ones The results indicated that the tests on infected leaves with strain Xaj 762 untreated with bacteriophage presented black coloring in the puncture site and little progress of the disease from the inoculation site (2-3 mm), bacteria was recovered from all from inoculated leaves. When Θ6 and Θ4.1 bacteriophages (deposit number PCM F/00087), are applied independently, a black-brown coloring is observed only in the inoculation site, also, no presence of the Xaj 762 strain was detected. The brown coloring in the inoculated site would be explained by the mechanical damage generated to get the bacteria to penetrate the tissue, because the controls presented the same signs without presence of Xaj. A similar result was observed when only ⊖36 phage was used. In the group inoculated only with the bacteria, little progression of the disease was observed, but a high Xaj load was present. (FIG. 13-A), not j when the ⊖36 phage and Xaj were used, the presence of bacteria was only in some leaflets and with low load (FIG. 13-B). There was no presence of the bacteria in controls (FIG. 13-C).

B. Determination of Phage Protection Against Xaj in Snuff Leaves (Mixture of Bacteriophages)

The snuff (*Nicotiana tabacum*) is a model plant that is used for virulence studies of *X. arboricola* pv *juglandis* (Bandi, et al. 2014). The challenge of protecting against phage consisted in an artificial inoculation of the *X. arboricola* pv *juglandis* bacteria through infiltration by stomas in snuff leaves. The bactericidal activity of bacteriophages on the pathogenic bacteria was evaluated this way. The design of snuff plants test is described below:

Snuff plants (*Nicotiana tabacum*) germinated in laboratory conditions were used, to make sure they are pathogens free.

Three groups were made: medium and phages safety controls; Xaj mixture infected group with; mixture of bacteria (strains Sag, Sag642 and Xaj10) and bacteriophage group ages. The groups were constituted by three snuff plants, and three secondaries leaves of each one were used. Each leaf was infiltrated in 4 sites. The mixture was of seven bacteriophages was infiltrated and inoculated with a mixture of three virulent strains of *Xanthomonas arboricola* pv *juglandis* infiltrated. Positive controls of infection and safety were inoculated only with pathogenic bacteria and bacteriophages respectively. The plants were left at room temperature for ten days.

Walnut blight signs development and presence of bacteria in the infiltrated areas were analyzed. Results were compared between groups of treated plants with bacteriophage and untreated ones. Re-isolation of *X.* pv *arboricola juglandis* was performed from infected leaves with disease signs, to determine the presence of the infection and if it was caused by the inoculated pathogenic bacteria.

Figure 14A:
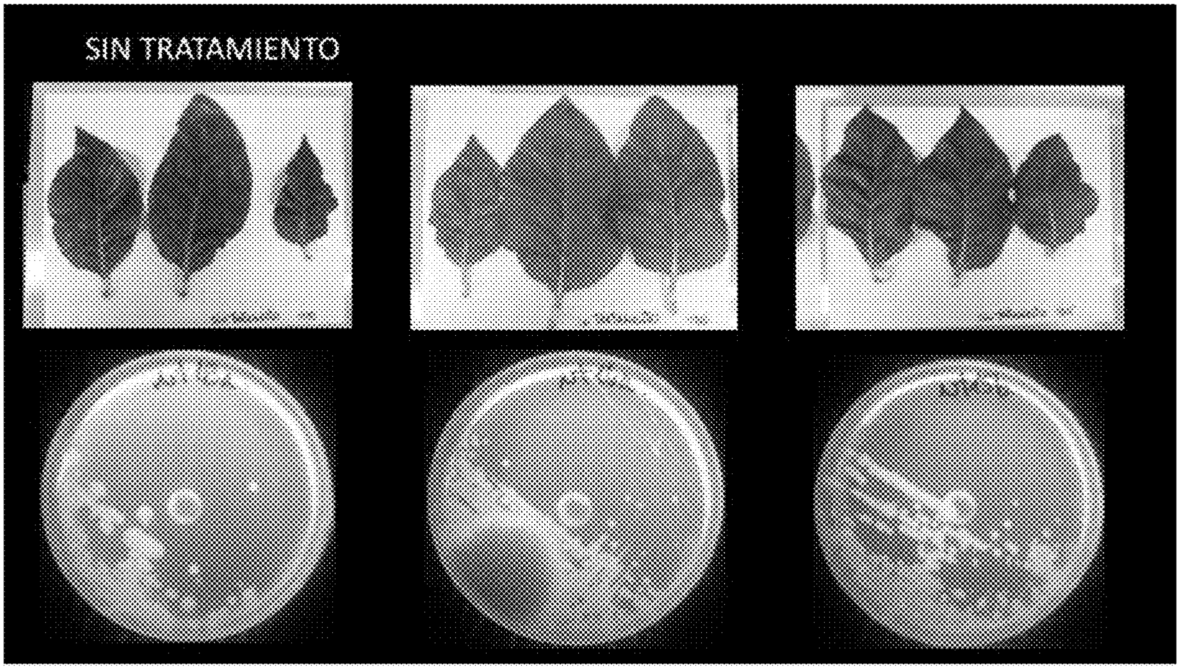
FIG. 14: Result of efficiency of the seven phages in controlling Xaj in snuff leaves (*Nicotiana tabacum*) evaluation. Disease signs and re-isolation of the bacteria (leaf infiltration method) are shown. A: Group Only with Xaj; B: Group treated with phage; C Medium control safety.
Figure 14B:
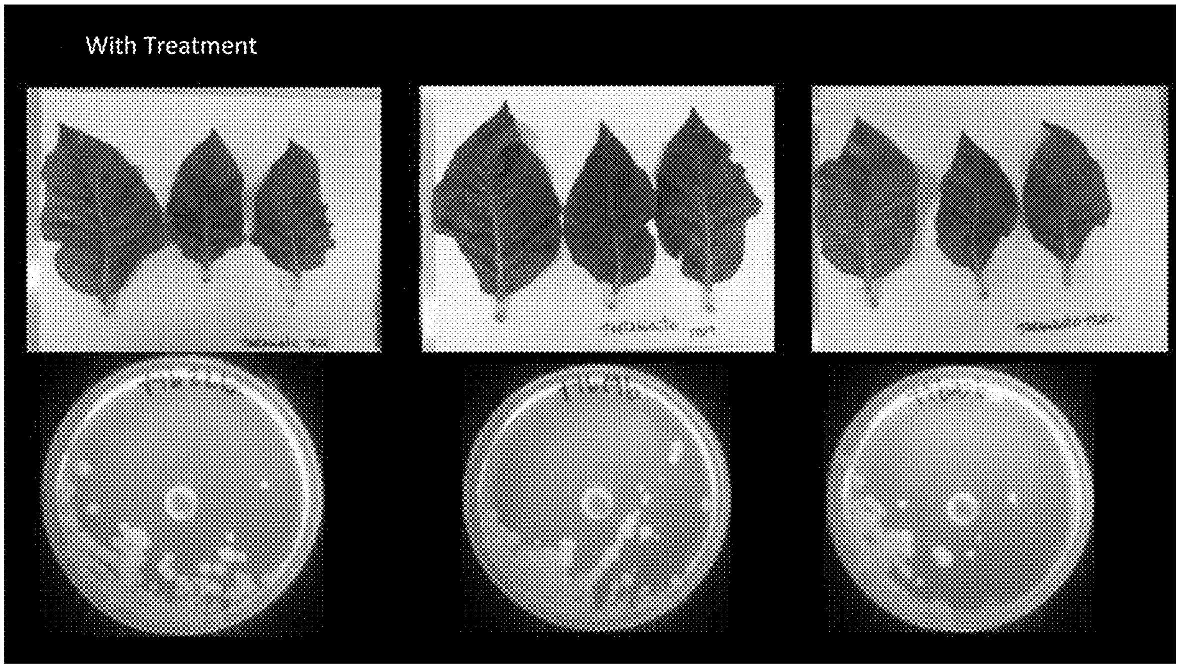
Figure 14C:
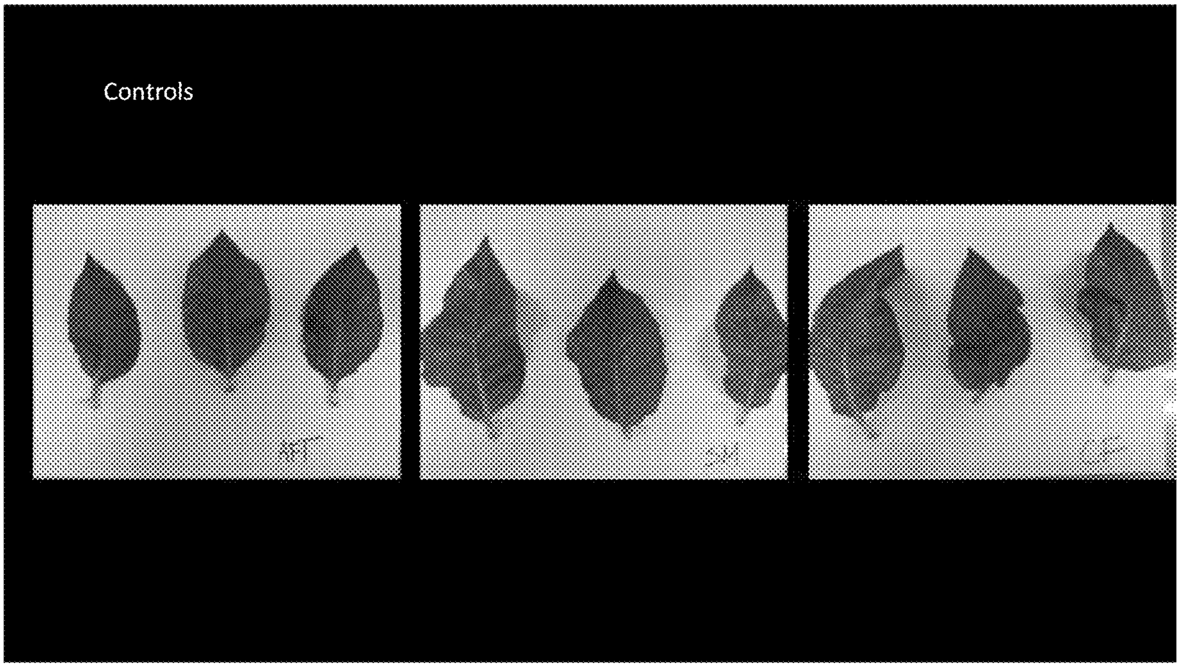

The results indicated that the group that only had *X.* pv *arboricola juglandis* strains presented disease signs in all plants (chlorotic, yellow and thinning areas in the infiltration site). Also, Xaj bacteria was present on all sheets (FIG. 14-A). On the other hand, plants that were infiltrated with the mixture of bacteriophages and bacteria had no disease signs. When the presence of Xaj was determined, it was only recovered in some of infiltration sites and at a very low load, only the presence of other bacteria not associated with the disease was observed (FIG. 14-B). Finally, no control presented disease signs nor presence of pathogenic bacteria (FIG. 14-C).

C. Determination of Phage Protection Against Xaj in Walnut Leaves (Mixture of Bacteriophages)

It consisted mainly in an artificial inoculation of bacteria *X.* pv *arboricola juglandis* mixture through infiltration by stomas in asymptomatic and walnut blight free walnut leaves, which were used to evaluate the bactericidal activity of the bacteriophages. The test was carried out in walnut trees as described below:

Free of Walnut Blight signs trees were choosen to be used in protection trials of bacteriophages against *X. arboricola* pv *juglandis*. Branches were selected in west direction in order to promote the bacteria infection through management of environmental conditions. The third leaflet of walnut leaves was selected to be inoculated (infiltration). Four groups were formed: two medium and phages safety controls; infected group only with a mixture of Sag, Sag642 and Xaj10 strains; and mixtures infected group with the bacteria and seven bacteriophages. For each group, two leaves by branch were infiltrated in triplicate, performing two infiltrations in the selected leaflets of each leaf. The mixture of the seven bacteriophages was infiltrated at a concentration of ($10^9$ PFU/mL total), and in turn inoculated with *X. arboricola* pv. *juglandis* ($10^8$ CFU/mL). Positive controls of infection and safety were inoculated only with pathogenic bacteria and bacteriophages respectively. As safety controls bacteriophages mixture and medium were inoculated. The branches were wrapped with plastic bags covered with aluminum foil in order to achieve high humidity and heat, the test was performed for ten days. Walnut Blight development signs and the presence of bacteria in the infiltrated areas were analyzed. Results were compared between groups of treated and untreated fruits bacteriophages Re-isolation of *X.* pv *arboricola juglandis* was performed from infected leaves with disease signs to determine the presence of the infection and if it was caused by the inoculated pathogenic bacteria.

Figure 15A:
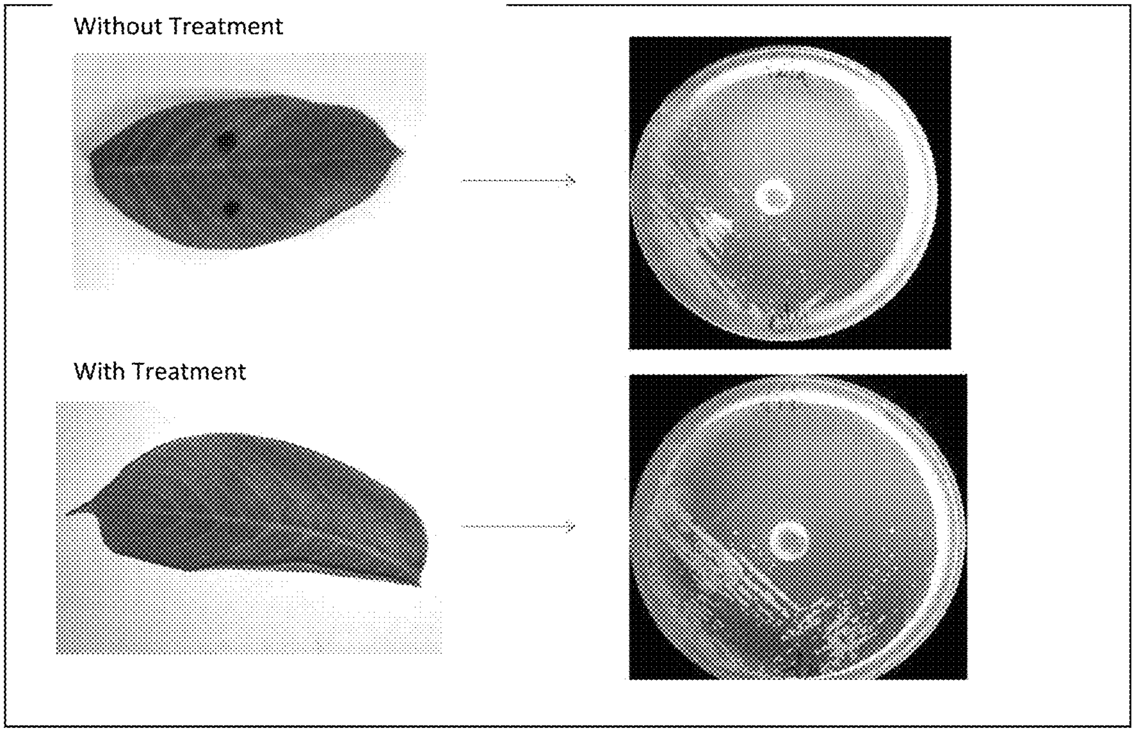
FIG. 15: Result of efficiency of the seven phages mixture in controlling Xaj in walnut leaves evaluation. Disease signs and re-isolation of the bacteria (leaf infiltration method) are shown. A, B and C are different trees held in test.
Figure 15B:
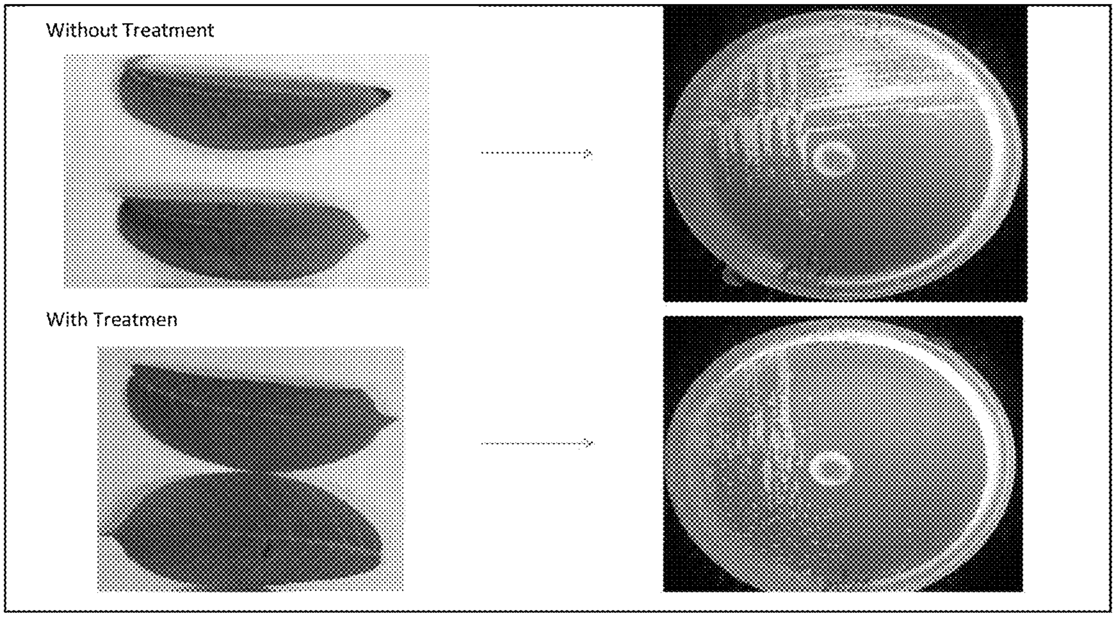
Figure 15C:
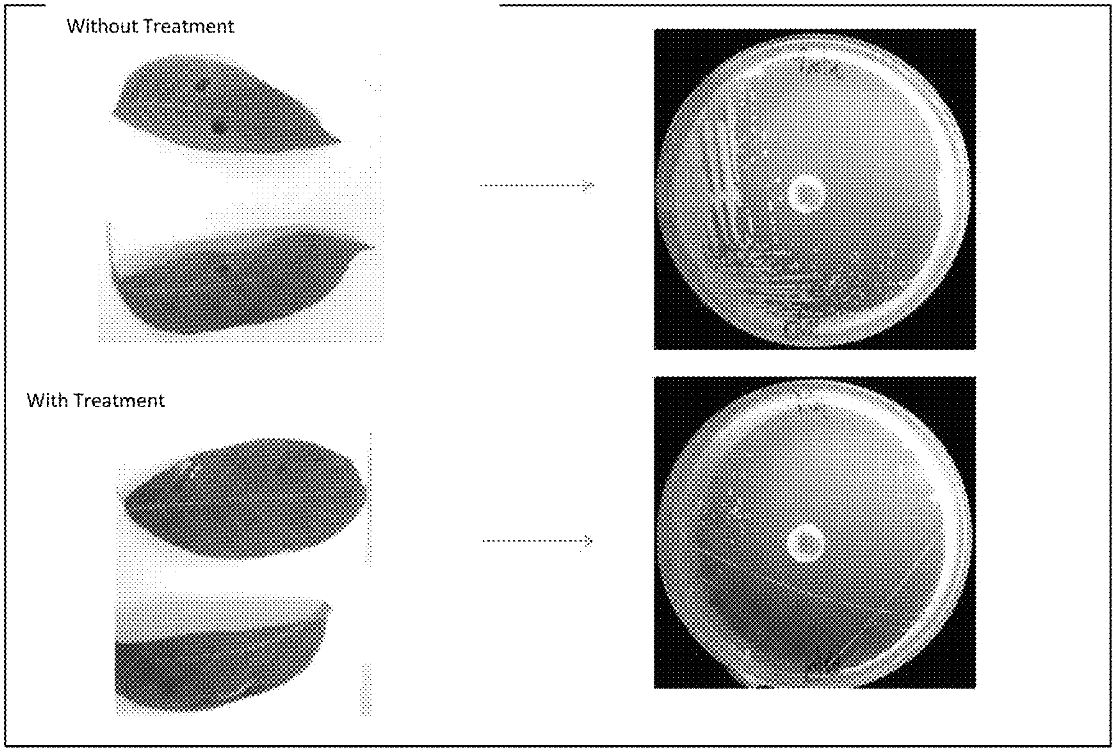

The results indicated that in untreated group, infected with the mixture of three Xaj strains (XajSag, Xaj10, Sag642), a damage between 75 to 100% of necrosis in the infiltration site was observed; bacteria were recovered from all the inoculated leaves (FIG. 15). When the mixture of the 7 bacteriophages (with treatment) was applied, a damage between 0 to 25% was observed, and the bacteria was only present in some of the infiltration sites in low concentration (FIG. 15). No control presented disease signs.

Example 8

Determination of Phage Inactivation by Exposure to Different Temperatures and Storage Types.

Figure 18:
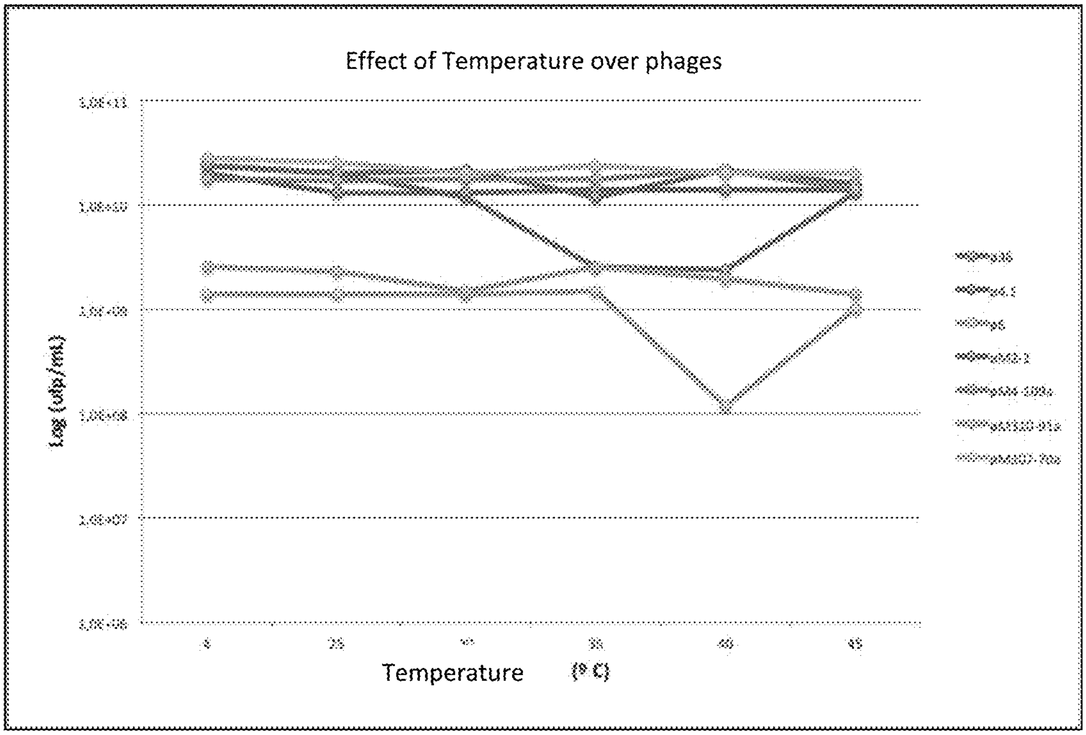
FIG. 18: Determination of temperature effect on the viability of the phage. The graph shows the inactivation degree inactivation of the seven selected phages, for a temperature range between 4° C.-45° C.

5 ml of each phage was incubated at temperatures of 4° C., 25° C., 30° C., 35° C., 40° C. and 45° C. for 15 min. Then, the title for each phage was quantified at the mentioned the temperatures, the titles of seven phages remained at the same log for the six tested temperatures (FIG. 18).

Figure 19:
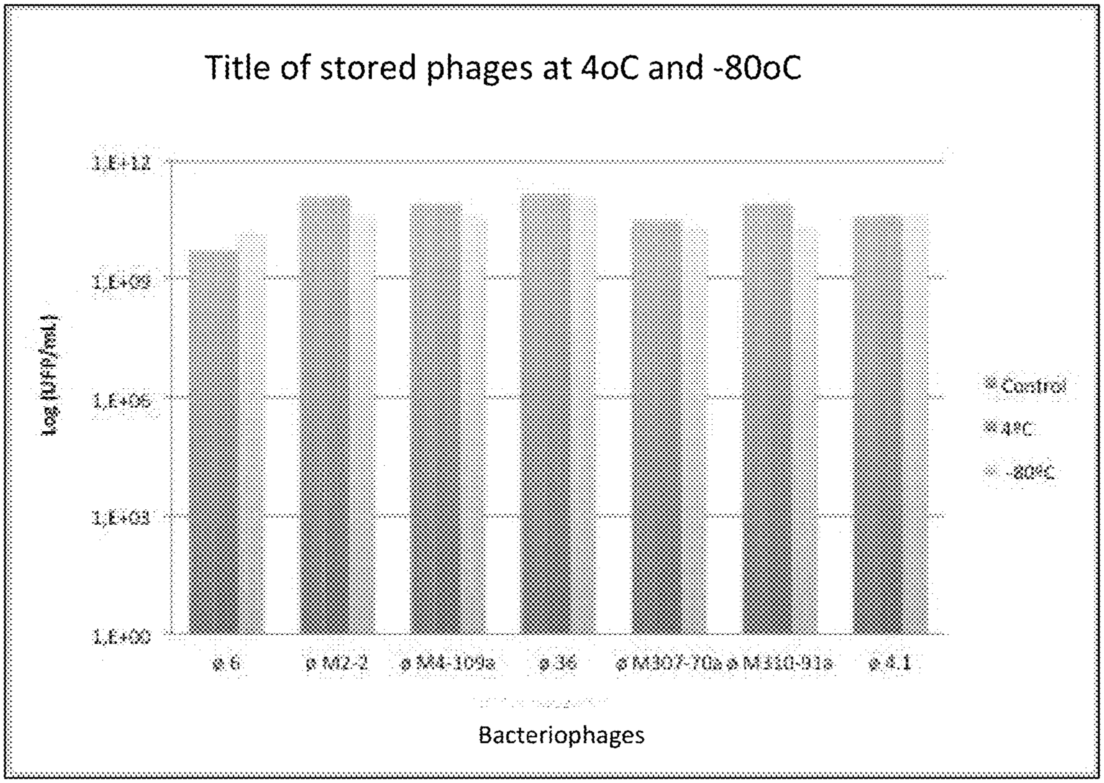
FIG. 19: Determination of phages storage type effect. The graph shows the degree of inactivation of the seven selected phages, when stored at −80° C. and 4° C.

The bacteriophage stocks were stored for four months at temperatures −80° C. and 4° C. After this time, the titles were compared with the original concentrations of phages (FIG. 19). Both methods were optimal for bacteriophages storage.

Example 9

Determination of Phage Inactivation by Exposure to Ionic, Compounds (Metallic and Nonmetallic) Used in Agrochemicals.

Compounds such as copper, iron, zinc, magnesium, manganese, boron, molybdenum, calcium, nitrogen, sulfur, phosphorus and potassium are used as biocides for controlling diseases, as fertilizers or as stimulants in the agricultural field.

Figure 20:
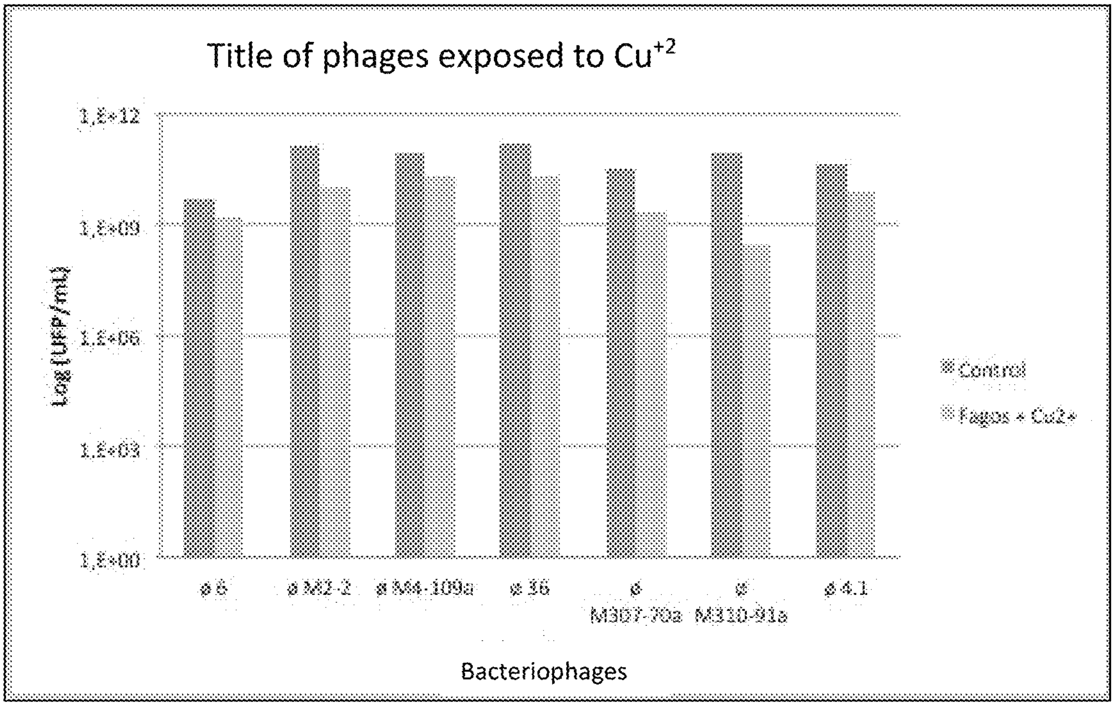
FIG. 20: Determination of phages inactivation by exposure to copper ion. The graph shows the inactivation degree of the seven selected phage, when exposed to a solution of copper sulfate (64 mg/mL).
Figure 21:
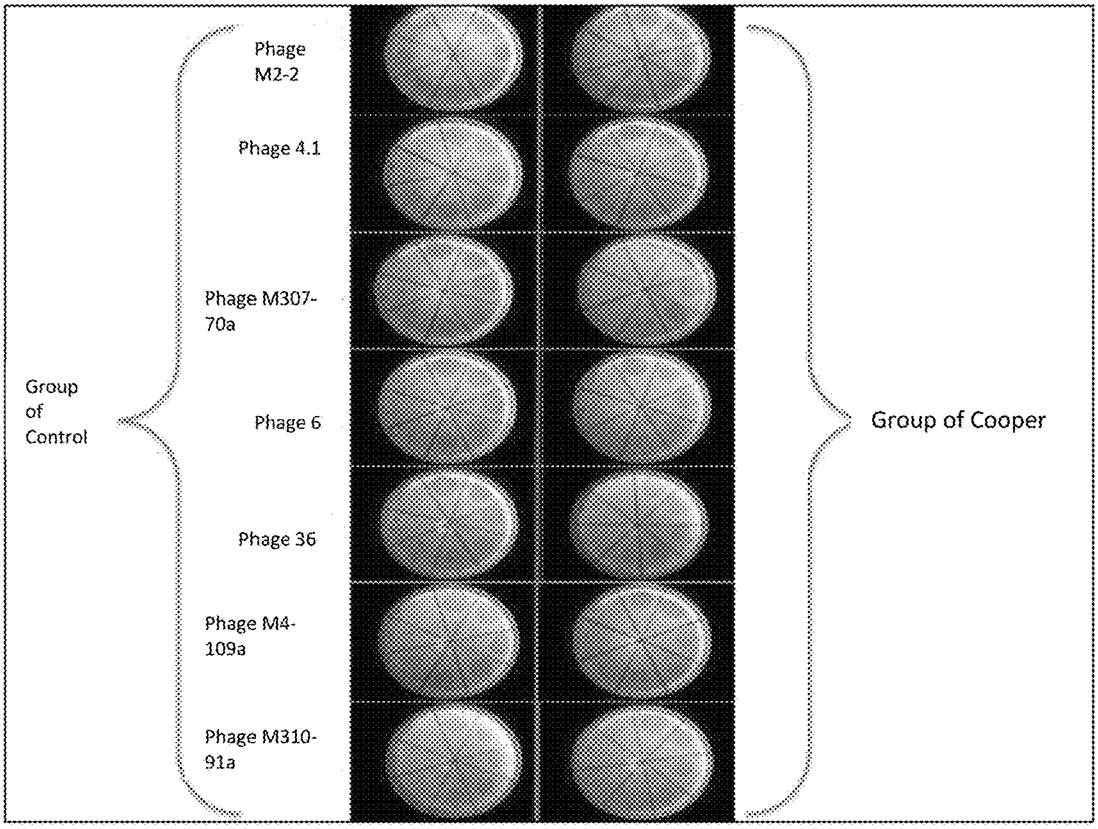
FIG. 21: Comparison of lysing capacity of the seven bacteriophages when exposed to copper.

Phages were exposed individually to an aqueous solution of copper sulfate (64 mg/mL). 100 uL of phage was mixed with 900 uL of the copper solution and was incubated for 20 minutes. The, the phages were washed with 1.5 mL of SM buffer through Amicon filtration (100K) and graduate system (FIG. 21). None of the phage was inactivated when exposed to copper (FIG. 20).

Example 9

Determination of Phage Inactivation by Exposure to UV Photoprotection.

Figure 22:
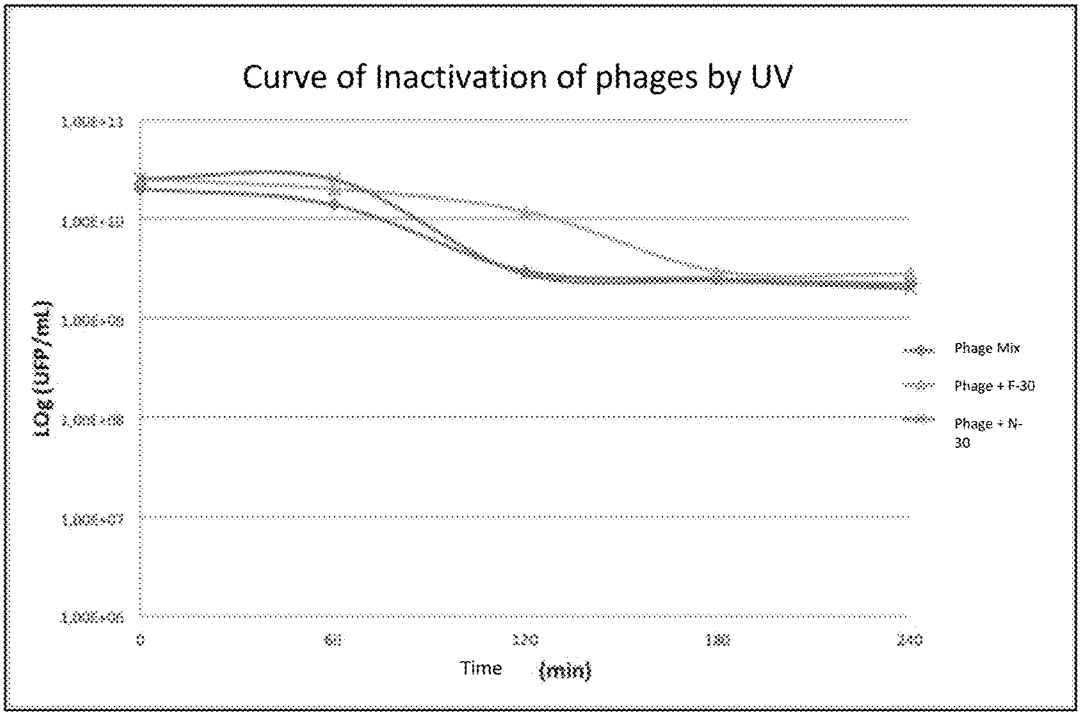
FIG. 22: Determination of phages inactivation by exposure to solar radiation. The graph depicts the degree of phages mixture inactivation, when exposed to direct sunlight.

The mixture of bacteriophages ($10^{10}$ PFU/mL of each one) was exposed to direct sunlight for 6 hours. Two preparations of phages mixtures were added separately to formulations F-30 and N-30, in order to evaluate the photoprotective effect. The results are shown in FIG. 22.

We claim:

1. Bactericidal composition against *Xanthomonas arboricola pv juglandis* for plants or parts thereof comprising a mixture of isolated bacteriophages consisting of bacteriophage deposited under deposit number PCM F/00087 (Theta4.1), bacteriophage deposited under deposit number PCM F/00088 (Theta6), bacteriophage deposited under deposit number PCM F/00089 (Theta36), bacteriophage deposited under deposit number PCM F/00090 (ThetaM4-109a), bacteriophage deposited under deposit number PCM F/00092 (ThetaM307-70a), bacteriophage deposited under deposit number PCM F/00091 (ThetaM310-91a) and bacteriophage deposit number PCM F/00093 (ThetaM2-2).

2. The bactericidal composition of claim 1, further comprising a buffer, a stabilizing agent or a mixture thereof.

3. The bactericidal composition of claim 2, wherein said buffer comprises one or more of the following components: NaCl, $MgSO_4$, Tris-HCl, gelatin at pH 7.5.

4. The bactericidal composition of claim 2, wherein said stabilizing agent is a salt that maintains osmotic pressure and as cofactors for phage absorption.

5. The bactericidal composition of claim 1 having stability at a temperature range between 4° C to 45° C.

6. The bactericidal composition of claim 1 comprising a bacteriophage concentration of $10^9$ PFU/mL.

7. A method for treating and/or protecting plants from infection by *Xanthomonas* pv *juglandis* resistant to copper or copper resistant walnut blight, comprising applying the bactericidal composition of claim 1 in the leaves, fruits and buds of a plant.

8. The method of claim 7 wherein said plant is a walnut.

9. The method of claim 7 wherein said plant is a tree.

10. The method of claim 9 wherein said tree is a walnut or pit.

11. The method of claim 7 wherein said plant is snuff.

* * * * *